US006354134B1

(12) United States Patent
Katafuchi et al.

(10) Patent No.: US 6,354,134 B1

(45) Date of Patent: Mar. 12, 2002

(54) OXYGEN SENSING ELEMENT USED IN A OXYGEN SENSOR

(75) Inventors: Tooru Katafuchi, Kariya; Kiyomi Kobayashi, Kuwana; Namitsugu Fujii, Yokkaichi; Hiromi Sano, Nagoya, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/196,129

(22) Filed: Nov. 20, 1998

(30) Foreign Application Priority Data

| | | |
|---|---|---|
| Nov. 20, 1997 | (JP) | 9-337869 |
| Sep. 4, 1998 | (JP) | 10-251054 |

(51) Int. Cl.$^7$ .......................... G01N 27/46; G01N 27/58

(52) U.S. Cl. .......................................... 73/23.32; 60/276

(58) Field of Search ............................ 73/23.31, 23.32, 73/116, 118.1, 31.05; 60/276

(56) References Cited

U.S. PATENT DOCUMENTS

| | | | | | |
|---|---|---|---|---|---|
| 3,978,006 A | | 8/1976 | Topp et al. | 252/477 R |
| 4,127,463 A | | 11/1978 | Rohr et al. | |
| 4,155,827 A | | 5/1979 | Maurer et al. | |
| 4,535,316 A | * | 8/1985 | Wertheimer et al. | 73/23.32 |
| 5,602,325 A | * | 2/1997 | McClanahan et al. | 73/23.31 |
| 5,616,825 A | * | 4/1997 | Achey et al. | 73/23.31 |
| 5,739,414 A | * | 4/1998 | Paulus et al. | 73/23.31 |
| 5,804,050 A | * | 9/1998 | Hayakawa et al. | 73/23.32 |
| 5,886,248 A | * | 3/1999 | Paulus et al. | 73/23.31 |
| 5,889,196 A | * | 3/1999 | Ueno et al. | 73/23.31 |

FOREIGN PATENT DOCUMENTS

| | | |
|---|---|---|
| DE | 2 206 216 | 8/1973 |
| DE | 28 38 122 | 3/1980 |
| DE | 37 26 479 A1 | 2/1989 |
| DE | 197 02 096 A1 | 7/1997 |
| EP | 0 811 840 A2 | 12/1997 |
| JP | 58-73857 | 5/1958 |
| JP | 1-170846 | 7/1989 |
| JP | 4-157358 | 5/1992 |
| JP | 5-126789 | 5/1993 |
| JP | 8-271474 | 10/1996 |

* cited by examiner

*Primary Examiner*—George Dombroske

(74) *Attorney, Agent, or Firm*—Pillsbury Madison & Sutro LLP

(57) ABSTRACT

A solid electrolytic body has an inside space serving as a reference gas chamber. A sensing electrode and a reference electrode are formed on the surface of the solid electrolytic body. A heater is disposed in the reference gas chamber. A contact portion comprises a region where the heater is brought into contact with the inner surface of the solid electrolytic body and an opposing region on the outer surface of the solid electrolytic body. The sensing electrode includes at least part of the contact portion. A gas receiving surface region, exposed to the measuring gas, extends from an element tip to a position spaced by a distance L away from the element tip. At least part of the contact portion is located in a region extending from the element tip to a position spaced by a distance 0.4L away from the element tip. The sensing electrode is entirely located in a region extending from the element tip to a position spaced by a distance 0.8L away from the element tip.

14 Claims, 21 Drawing Sheets

OXYGEN SENSING ELEMENT USED IN A OXYGEN SENSOR

BACKGROUND OF THE INVENTION

The present invention relates to a heater-equipped oxygen sensing element which is preferably installed in an internal combustion engine to detect the concentration of oxygen gas involved in the exhaust gas and control an air-fuel ratio of the internal combustion engine.

To control the air-fuel ratio, internal combustion engines have oxygen sensing elements provided in their exhaust passages.

For example, a conventional oxygen sensing element comprises a cup-shaped solid electrolytic body having an inside space serving as a reference chamber, a sensing electrode provided on an outer surface of the solid electrolytic body so as to be exposed to measuring gas, and a reference electrode provided on an inner surface of the solid electrolytic body. The sensing electrode and the reference electrode may extend entirely or partly on the inner and outer surfaces of the solid electrolytic body (refer to Unexamined Japanese Patent Application No. SHO 58-73857).

Furthermore, an electric heater is disposed in the reference chamber. This kind of oxygen sensing elements do not operate properly until their temperature reaches a predetermined temperature level. Thus, the heater is usually equipped to quickly increase the temperature of the oxygen sensing element when the ambient temperature is low, thereby reducing a deactivated duration and correctly measuring the oxygen concentration.

However, this kind of conventional oxygen sensing elements have the following problems.

The outer surface of the oxygen sensing element has a gas receiving surface region extending from a distal end of the sensing element to a position spaced by a distance L away from the distal end of the sensing element. The gas receiving surface region is exposed to the measuring gas whose temperature increases to a higher temperature level during the operation of this sensing element.

When the sensing electrode and the reference electrode are formed entirely on the outside and inside surfaces of the solid electrolytic body, the oxygen sensing element produces a sensor signal equivalent to a composite output from a plurality of electric circuits sequentially arranged from a high-temperature section to a low-temperature section along an entire surface of the solid electrolytic body. When the oxygen sensing element has a low-temperature portion, its sensor output and response will deteriorate due to insufficient activation at the low-temperature portion.

Furthermore, similar problems may arise even when the sensing electrode and the reference electrode are formed partly on the outer and inner surfaces of the solid electrolytic body. For example, when these electrodes are located in the low-temperature region, the sensor will produce an inaccurate sensor output due to insufficient activation at the low-temperature portion.

The oxygen sensing elements, when installed in the exhaust passage of an internal combustion engine, need to produce an accurate sensor output within a short period of time after the internal combustion engine starts its operation. To satisfy this requirement, the oxygen sensing elements must operate properly with a short dead time which is required for the heater to increase the temperature of the solid electrolytic body to a predetermined active level. These requirements were difficult goals to attain for the conventional oxygen sensing elements.

SUMMARY OF THE INVENTION

In view of the conventional problems, the present invention has an object to provide an oxygen sensing element that is rapid in activation and excellent in response.

To accomplish this and other related objects, one aspect of the present invention provides an oxygen sensing element comprising a cup-shaped solid electrolytic body with one end closed and an inside space serving as a reference gas chamber, a sensing electrode provided on an outer surface of the solid electrolytic body so as to be exposed to measuring gas, a reference electrode provided on an inner surface of the solid electrolytic body, and a heater disposed in the inside space of the reference gas chamber. A contact portion comprises a region where the heater is brought into contact with the inner surface of the solid electrolytic body and an opposing region on the outer surface of the solid electrolytic body. The sensing electrode includes at least part of the contact portion. A gas receiving surface region, exposed to the measuring gas when the oxygen sensing element is operated, is provided on the outer surface of the oxygen sensing element so as to extend from a distal end of the oxygen sensing element to a position spaced by a distance L away from the distal end of the oxygen sensing element. At least part of the contact portion is located in a region extending from the distal end of the oxygen sensing element to a position spaced by a distance 0.4L away from the distal end of the oxygen sensing element. And, the sensing electrode is entirely located in a region extending from the distal end of the oxygen sensing element to a position spaced by a distance 0.8L away from the distal end of the oxygen sensing element.

With this arrangement, the inner surface is brought into contact with the heater at the contact portion. The sensing electrode includes at least part of the contact portion. FIG. 5 shows the contact portion including an inner point "Pi" where the heater is brought into contact with the inner surface of the solid electrolytic body and an outer point "Po" opposing the inner point "Pi" via the solid electrolytic body, together with a neighboring region including the vicinity of these points "Pi" and "Po."

The contact portion on the inner surface may be a point (or points), a line (or lines), or a surface (or surfaces) which depends on the contact condition between the heater and the inner surface. The heater may be brought into contact with the inner surface at a single portion or a plurality of portions.

The gas receiving surface region is directly exposed to the measuring gas when the oxygen sensing element is operated. The gas receiving surface region has a neighbored surface region that is not exposed to the measuring gas. A clearance between the gas receiving surface region and the neighbored surface region is sealed by a packing, such as a metallic spring, which is capable of preventing gas leakage.

At least part of the contact portion is located in the region extending from the distal end of the oxygen sensing element to the position spaced by the distance 0.4L away from the distal end of the oxygen sensing element. If the contact portion is located at an altitudinal level higher than this region, heat leakage toward the upper low-temperature region of the oxygen sensing element will increase. This will result in insufficient temperature increase at the contact portion. Activation of the oxygen sensing element will be delayed.

The sensing electrode is entirely located in the region extending from the distal end of the oxygen sensing element to the position spaced by the distance 0.8L away from the distal end of the oxygen sensing element. If the sensing electrode is not completely located in this region, the sensing electrode temperature may decrease locally. Such a local temperature reduction will result in deteriorated response in the sensor performance.

The heater includes a resistor element generating heat in response to supplied electric power. It is preferable that the heat-generating resistor element opposes the measuring electrode. With this arrangement, it becomes possible to effectively heat the sensing electrode, enhancing the activity of the oxygen sensing element.

The oxygen sensor of the present invention operates in the following manner. The inner surface of the oxygen sensing element is brought into contact with the heater at the contact portion. The sensing electrode includes at least part of the contact portion.

Heat generated from the heater is directly transmitted to the sensing electrode via the inner surface and the solid electrolytic body. Thus, the sensing electrode is directly heated by the heater. Accordingly, the present invention reduces the activation time required from initiation of heating by the heater to generation of an accurate sensor signal from the activated sensing element.

The contact portion is located in the region extending from the distal end of the oxygen sensing element to the position spaced by the distance 0.4L away from the distal end of the oxygen sensing element. With this arrangement, it becomes possible to reduce the heat leakage toward the upper low-temperature region of the oxygen sensing element. Thus, the heating efficiency is improved.

The sensing electrode is entirely located in the region extending from the distal end of the oxygen sensing element to the position spaced by the distance 0.8L away from the distal end of the oxygen sensing element. Thus, the sensing electrode can maintain a high temperature during operation of the sensing element (refer to FIG. 8), realizing uniform temperature distribution and satisfactory response. The activation time is shortened.

The present invention provides an oxygen sensing element rapid in activation and excellent in response.

As the sensing electrode is partly provided on the solid electrolytic body, the total cost for the electrode is low compared with a case where the electrode is entirely formed on the surface of the solid electrolytic body.

The sensing electrode may be formed at the distal end of the sensing element, or may be formed along a cylindrical side portion of the sensor body other than the distal end as shown in FIG. 15.

It is preferable that the electrode area is larger than 2 $mm^2$. If the electrode area is less than 2 $mm^2$, an obtained sensor output will be insufficient.

According to the present invention, it is preferable that sensing electrode and the reference electrode are in a confronting relationship via the solid electrolytic body.

The sensor output is obtained when oxygen ion current flows between the sensing electrode and the reference electrode. From the functional view point, a portion of the electrode can be omitted if this portion is offset from an opponent electrode. Both the sensing electrode and the reference electrode are made of a noble metal or the like.

Accordingly, the present invention reduces the total amount of the electrode material and therefore reduced the total cost of the oxygen sensing element.

According to the present invention, it is preferable that an external lead electrode extends on the outer surface of the solid electrolytic body to transmit a sensing signal of the sensing electrode to the outside, and the external lead electrode has a circumferential width in a range from 0.1 mm to 5 mm.

The external lead electrode shrinks when it is exposed to the high-temperature gas. If the width of the external electrode is less than 0.1 mm, the external lead electrode may be broken due to the progress of shrinkage.

On the other hand, if the width of the external electrode exceeds 5.0 mm, the sensor output and response may deteriorate due to the influence of the low-temperature portion of the external lead electrode.

It is possible to provide a plurality of external lead electrodes, since the total number of the external lead electrodes is not limited to a specific number. In this case, it is preferable that the sum of the widths of the plurality of external lead electrodes is less than 5.0 mm.

The external lead electrode can be formed by plating, paste printing, sputtering, or evaporation.

According to the present invention, it is preferable that an internal lead electrode extends on the inner surface of the solid electrolytic body to transmit a reference signal of the reference electrode to the outside, and the internal lead electrode and the external lead electrode are in an offset relationship via the solid electrolytic body.

This offset arrangement is effective to reduce the oxygen ion current flowing between the internal lead electrode and the external lead electrode. Adverse influence given to the sensor output is reduced, and the response of the oxygen sensing element is improved.

According to the present invention, it is preferable that the sensing electrode is formed by chemical plating.

In general, chemical plating, conductive paste printing, sputtering or evaporation is preferably used in the formation of various electrodes.

The electrode formed by the chemical plating has excellent surface energy and catalytic activity because of a sintering temperature lower than that of the paste electrode. The response is higher.

Furthermore, compared with the electrode formed by sputtering or evaporation, the electrode formed by the chemical plating has numerous fine pores which contribute the diffusion of oxygen and therefore improve the response.

Prior to the chemical plating, a noble metallic nucleus of a predetermined pattern is provided on the outer surface of the solid electrolytic body. Subsequently, the chemical plating is performed on the solid electrolytic body to form an electrode having the same pattern as that of the noble metallic nucleus. Even a complicated sensing electrode can be easily formed.

The noble metallic nucleus is formed in the following manner.

An organo-metallic paste containing a noble metal is printed in a predetermined pattern on the surface of the solid electrolytic body. Then, heat treatment is performed to remove the binder and decompose the noble metal containing organometal, thereby forming the noble metallic nucleus by the noble metal depositing on the surface.

The organometallic paste may contain a di-benzylidene platinum. The noble metal may be Pt, Pd, Au, or Rh.

The reference electrode may be formed by chemical plating, conductive paste printing, sputtering or evaporation.

Furthermore, the present invention has an object to provide an oxygen sensing element excellent in response and in thermal durability.

To accomplish this and related objects, another aspect of the present invention provides an oxygen sensing element comprising a solid electrolytic body, a reference gas chamber provided in the solid electrolytic body, a sensing electrode provided on an outer surface of the solid electrolytic body, a reference electrode provided on an inner surface of the solid electrolytic body which defines the reference gas chamber. A gas receiving surface region, exposed to measuring gas when the oxygen sensing element is operated, is provided on the outer surface of the oxygen sensing element so as to extend from a distal end of the oxygen sensing element to a position spaced by a distance L away from the distal end of the oxygen sensing element. The sensing electrode has a length L1 equal to or larger than 0.2L in a longitudinal direction of the oxygen sensing element. The sensing electrode is entirely located in a region extending from the distal end of the oxygen sensing element to a position spaced by a distance 0.8L away from the distal end of the oxygen sensing element. And, the sensing electrode has a thickness of 0.5~3.0 $\mu$m.

According to this arrangement of the present invention, the sensing electrode has the length L1 equal to or larger than 0.2L in the longitudinal direction of the oxygen sensing element. The sensing electrode is entirely located in the region extending from the distal end of the oxygen sensing element to the position spaced by the distance 0.8L away from the distal end of the oxygen sensing element. And, the sensing electrode has the thickness of 0.5~3.0 $\mu$m. The distal end of the oxygen sensing element is an end portion protruding toward the measuring gas (refer to FIG. 19).

If the length L1 is less than 0.2L, the sensing electrode will shrink due to high-temperature heat and may cause the breaking. The sensor output and the response will be lowered.

A preferable upper limit of the length L1 is 0.8L. If the length L1 exceeds 0.8L, the sensor response may deteriorate.

If the thickness of the sensing electrode is less than 0.5 $\mu$m, the sensing electrode will shrink due to high-temperature heat and may cause the breaking. If the thickness is larger than 3.0 $\mu$m, the oxygen gas will not diffuse and penetrate well in the sensing electrode. Thus, the sensor response will be worsened.

According to the oxygen sensing element of the second aspect of the present invention, the length L1 of the sensing electrode is equal to or larger than 0.2L. This arrangement provides the sensing electrode having a sufficient area to prevent undesirable thermal shrinkage even when it is subjected to high-temperature gas for a long time. The breaking of the sensing electrode can be prevented. Thus, it becomes possible to provide an oxygen sensing element having excellent thermal durability.

The sensing electrode is entirely located in the region extending from the distal end of the oxygen sensing element to the position spaced by the distance 0.8L away from the distal end of the oxygen sensing element, when "L" represents the length of the gas receiving surface region where the solid electrolytic body is exposed to the sensing gas.

In general, the oxygen sensing element is assembled in an oxygen sensor. The oxygen sensor has a portion exposed to the measuring gas and a portion exposed to the reference gas. A metallic packing is provided to seal the boundary between them when the oxygen sensing element is installed. The metallic packing is adjacent to the edge of the gas receiving surface region on the oxygen sensing element, and prevents the measuring gas from advancing beyond this edge portion.

The measuring gas flows at a reduced speed in a region exceeding the 0.8L position due to the presence of the metal packing. If the sensing electrode is provided in this region, the sensor output will deteriorate.

Accordingly, it becomes possible to obtain an oxygen sensing element having satisfactory response by providing the sensing electrode in the region not exceeding the 0.8L position. In this case, the 0.8L position is included in the desirable region for the sensing electrode.

Furthermore, according to the present invention, the sensing electrode has the thickness of 0.5~3.0 $\mu$m. This arrangement makes it possible to allow the measuring gas to diffuse and penetrate well in the sensing electrode. Thus, it becomes possible to obtain an oxygen sensing element having excellent response.

According to the above-described arrangement of the present invention, it becomes possible to provide an oxygen sensing element excellent in response and thermal durability.

The oxygen sensing element of the present invention is applicable to a oxygen concentration cell type oxygen sensor or a limiting-current type oxygen sensor. The sensing electrode may be an electrode formed at the distal end region of the oxygen sensing element (refer to FIG. 19) or, alternatively, can be a ring electrode formed along an outer surface of the solid electrolytic body except the distal end (refer to FIG. 30). Furthermore, the ring electrode can be replaced by a partly provided electrode (refer to FIGS. 31A and 31B).

The sensing electrode and the reference electrode are connected to terminal portions via lead portions to transmit sensing and reference signals to the outside.

Each electrode and associated lead and terminal portions can be fabricated integrally. The reference electrode and associated lead and terminal portions can be fabricated by chemical plating, paste printing, sputtering, or evaporation. The sensing electrode and associated lead and terminal portions can be fabricated in the same manner by using the same method.

It is preferable that the sensing electrode is a noble metallic electrode including at least one noble metal having catalytic activity, for example, selected from the group consisting of Pt, Pd, Au and Rh.

It is preferable that the lead portion of the sensing electrode and the lead portion of the reference electrode are not in an opposed relationship (refer to FIG. 20B). With this arrangement, it becomes possible to prevent a low-temperature lead portion from giving an adverse influence to the sensor output, thereby improving the sensor response.

It is also preferable that the gas receiving surface region is covered by a single layer or a plurality of layers so that the gas receiving surface region is indirectly exposed to the measuring gas.

Furthermore, it is preferable that the oxygen sensing element has the heater which comprises the heat generating portion accommodating the resistor element generating heat in response to supplied electric power. The sensing electrode is positioned at the position opposing to at least the central position of the heat generating portion in the longitudinal direction of the oxygen sensing element. And, the heat generating portion has the length L2 in the longitudinal direction of the oxygen sensing element so as to satisfy the relationship $1.0 \leqq L1/L2 \leqq 4.0$.

As understood from later-described FIG. 23, the central position of the heat generating portion is a highest temperature portion. Disposing the sensing electrode at the position opposing to the central position of the heater is effective to increase the heating efficiency and the response of the heater.

When the heat generating portion satisfied the relationship $1.0 \leqq L1/L2 \leqq 4.0$, it becomes possible to provide an oxygen sensing element excellent in response and thermal durability.

If the ratio L1/L2 is smaller than 1.0, the sensing electrode may shrink when subjected to high-temperature environment heated by the heater.

On the other hand, if the ratio L1/L2 is larger than 4.0, the temperature distribution in the longitudinal direction of the sensing electrode will have a large temperature difference due to presence of a low-temperature region. The low-temperature region will give adverse influence to the sensor output and deteriorate the response.

The heater may have a rod body, a flat platelike body, or the like.

Furthermore, it is preferable that the heat generating portion has the length L2 in the range of 3~12 mm.

With this arrangement, the generated heat can be effectively transmitted to the distal end region of the oxygen sensing element. When the oxygen sensing element is used to detect the oxygen concentration in the exhaust passage of an automotive vehicle, a dead time of the oxygen sensor can be shortened. In this case, the dead time is a period of time required for the activation of the oxygen sensing element until the oxygen sensing element operates properly after the engine is started up.

If the length L2 is less than 3 mm, the resistor element will be short correspondingly. Accordingly, the resistor element will have an insufficient resistance value. Generated heat will be unsatisfactory.

On the other hand, if the length L2 is larger than 12 mm, it takes a long time to increase the temperature of the heater. In other words, activation time is long. The activation time is a period of time required for the oxygen sensing element to reach a predetermined activation temperature from an ordinary temperature. The oxygen sensing element can operate properly only when the temperature exceeds the activation temperature.

Furthermore, it is preferable that the length L of the gas receiving surface region is in the range of 15~30 mm. With this arrangement, it becomes possible to reduce the temperatures of neighboring metallic parts. This is advantageous when the oxygen sensor is installed in an automotive vehicle.

As described above, the oxygen sensing element is used as a component of an oxygen sensor. The inside space of the oxygen sensor is separated into a portion where the measuring gas flows and a portion where air serving as the reference gas flows. The boundary between two portions is sealed. The sealed portion is adjacent to the edge of the gas receiving surface region.

When the length L of the gas receiving surface region is less than 15 mm, the sealed portion is positioned closely to the heat generating portion of the heater. The temperature of the sealed portion will be increased to a higher value.

In general, the seal of the oxygen sensing element is an assembly of metallic members which are elastically deformable. Thus, there is the possibility that the sealed portion may deteriorate when the environmental temperature of the sealed portion exceeds the durable limit of the metallic members. The measuring gas will be mixed with the reference gas, rendering the detection of the oxygen concentration inaccurate.

On the other hand, if the length L is larger than 30 mm, enlarged covers will be required for covering the oxygen sensing element (refer to FIG. 23). The large-sized oxygen sensor is not desirable when an installation space is limited.

Furthermore, it is preferable that the sensing electrode is fabricated by chemical plating.

The sensing electrode fabricated by the chemical plating has excellent response. According to the chemical plating, the plating film is sintered at a low temperature. This is effective to form an electrode having a high surface energy and excellent catalytic activity.

In general, the electrode fabricated by chemical plating has numerous fine pores which improve the diffusibility of oxygen gas.

It is preferable to form a noble metallic nucleus of a predetermined pattern on the outer surface of the solid electrolytic element prior to the chemical plating. The noble metallic nucleus is formed in the following manner. An organometallic paste containing a noble metal is printed in a predetermined pattern on the surface of the solid electrolytic body. Subsequently, heat treatment is performed to remove the binder and decompose the noble metal containing organometal, thereby forming the noble metallic nucleus by the noble metal depositing on the surface.

Then, the chemical plating is applied on the solid electrolytic body to form an electrode having the same pattern as that of the noble metallic nucleus. According to this method, a complicated sensing electrode can be easily formed.

Furthermore, it is preferable that the reference electrode and the sensing electrode are in an opposed relationship via the solid electrolytic body. With this arrangement, it become possible to prevent the electrode containing expensive noble metals from being unnecessarily widened, thereby reducing the manufacturing cost.

Furthermore, it is preferable that the solid electrolytic body is a cup-shaped body having one end closed and having an inner space serving as the reference gas chamber, and the heater is accommodated in the reference gas chamber.

The present invention can be applied to a so-called cup-shaped oxygen sensing element.

Furthermore, it is preferable that a clearance of 0.05~1.0 mm is provided between the heater and the inner surface of the oxygen sensing element at the longitudinal position corresponding to the sensing electrode.

With this arrangement, the solid electrolytic body can be effectively heated by the heater.

If the clearance is larger than 1.0 mm, generated heat will not be effectively transmitted to the solid electrolytic body due to convection caused in the widened space between the solid electrolytic body and the heater.

On the other hand, if the clearance is less than 0.05 mm, the diffusibility of the oxygen gas will be worsened. The sensor output will decrease due to lack of oxygen gas.

Furthermore, it is preferable that the oxygen sensing element is a multilayered sensing element, and the heater and the solid electrolytic body are accumulated layers of the multilayered sensing element.

The present invention can be applied to the multilayered oxygen sensing element which comprises platelike integrated layers of the solid electrolytic body and the heater layers.

BRIEF DESCRIPTION OF THE DRAWINGS

The above and other objects, features and advantages of the present invention will become more apparent from the following detailed description which is to be read in conjunction with the attached drawings, in which.

DESCRIPTION OF THE PREFERRED EMBODIMENTS

Figure 1:
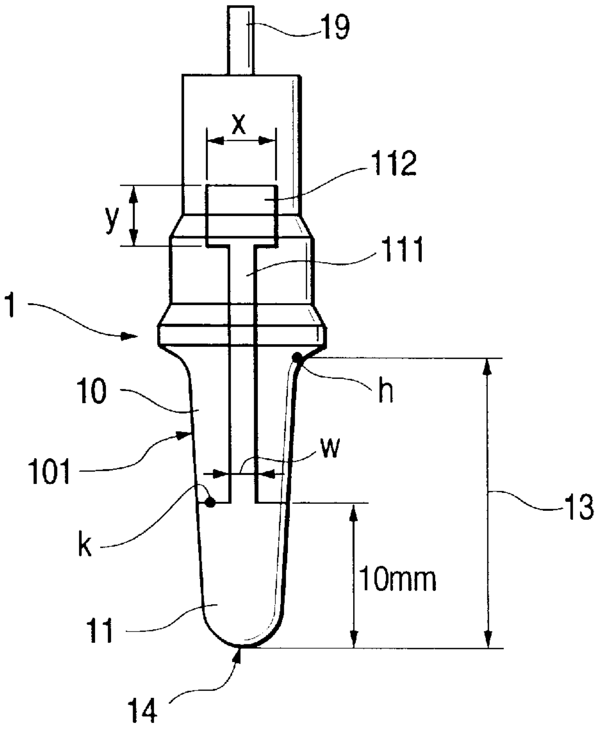
FIG. 1 is a side view showing an oxygen sensing element in accordance with a first embodiment of the present invention.

Preferred embodiments of the present invention will be explained hereinafter with reference to the attached drawings. Identical parts are denoted by the same reference numerals throughout the views.

First Embodiment

An oxygen sensor of a first embodiment of the present invention will be explained with reference to FIGS. 1 through 12.

As shown in FIGS. 1 through 5, an oxygen sensing element 1 of the first embodiment comprises a cup-shaped solid electrolytic body 10 having one end closed and an inside space serving as a reference gas chamber 18, a sensing electrode 11 provided on an outer surface 101 of the solid electrolytic body 10 so as to be exposed to measuring gas, a reference electrode 12 provided on an inner surface 102 of the solid electrolytic body 10, and a heater 19 disposed in the reference gas chamber 18.

Figure 5:
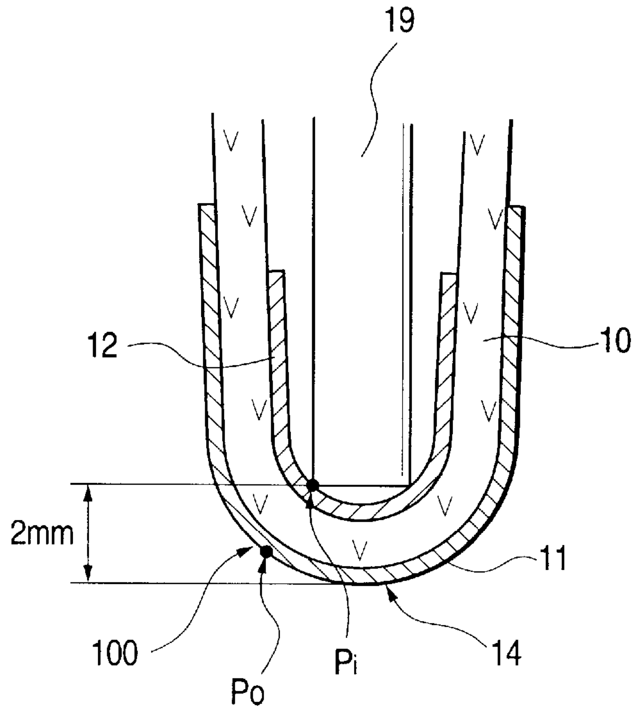
FIG. 5 is a cross-sectional view showing an essential arrangement of the oxygen sensing element in accordance with the first embodiment of the present invention.

FIG. 5 shows a contact portion 100 comprising a region where the heater 19 is brought into contact with the inner surface 102 of the solid electrolytic body 10 and an opposing region on the outer surface 101 of the solid electrolytic body 10. The sensing electrode 11 includes at least part of the contact portion 100.

Figure 2:
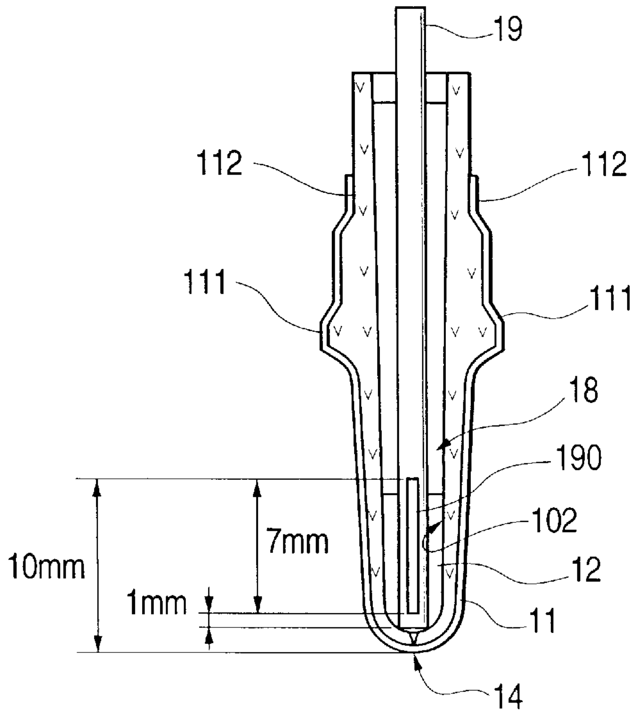
FIG. 2 is a vertical cross-sectional view showing the oxygen sensing element in accordance with the first embodiment of the present invention.
Figure 3:
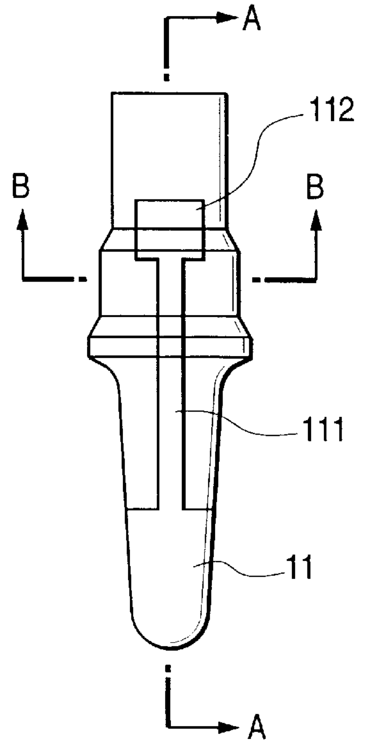
FIG. 3 is a side view showing a solid electrolytic body in accordance with the first embodiment of the present invention.

As shown in FIGS. 1, 2 and 5, the oxygen sensing element 1 has an outer surface (i.e. 101) including as a gas receiving surface region 13 exposed to the measuring gas when the oxygen sensor is operated. The gas receiving surface region 13 extends from an element tip 14 (i.e., a distal end of the oxygen sensing element 1) to a position spaced by a distance L away from the element tip 14. The contact portion 100 is located in a region extending from element tip 14 to a position spaced by a distance 0.4L away from the element tip 14.

Furthermore, as shown in FIG. 1, the sensing electrode 11 is entirely located in a region extending from the element tip 14 to a position spaced by a distance 0.8L away from the element tip 14.

A detailed arrangement of the oxygen sensing element 1 of the first embodiment will be explained hereinafter.

As shown in FIGS. 1 through 4, an external lead electrode 111 extends on the outer surface 101 of the solid electrolytic body 10 to transmit a sensing signal from the sensing electrode 11 to an external terminal electrode 112. An internal lead electrode 121 extends on the inner surface 102 of the solid electrolytic body 10 to transmit a reference signal from the reference electrode 11 to an internal terminal electrode 122.

The heater 19, having a rod body, is disposed in the reference gas chamber 18. The heater 19 accommodates a resistor element 190 generating heat in response to supplied electric power.

The solid electrolytic body 10 is made of $ZrO_2$ which is an oxygen ion conductive material.

According to this embodiment, the gas receiving surface region 13 of the solid electrolytic body 10 shown in FIG. 1 has an axial length of 18 mm (i.e., L=18 mm). The sensing electrode 11 is located in a range extending from the element tip 14 to a position spaced by 0.56 L (=10 mm) away from the element tip 14.

Figure 6:
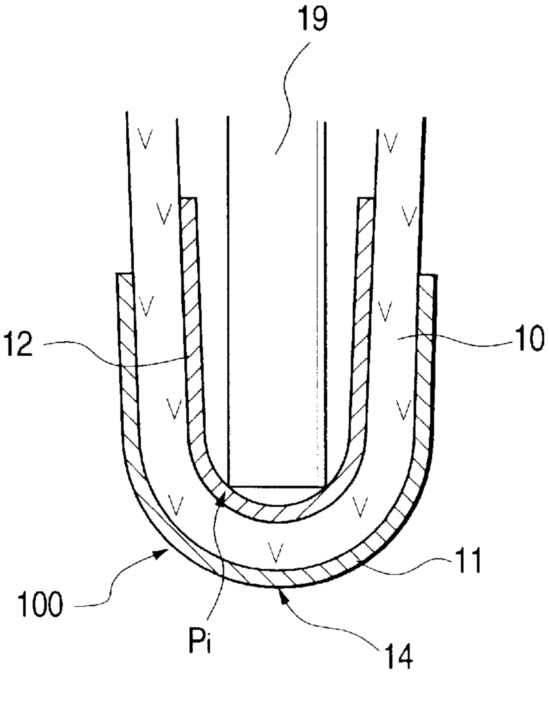
FIG. 6 is a cross-sectional view showing an essential arrangement of a modified oxygen sensing element in accordance with the first embodiment of the present invention.

The sensing electrode 11 and the reference electrode 12 are in a confronting relationship via the solid electrolytic body 10 as shown in FIG. 5. The reference electrode 12 is slightly shorter than the sensing electrode 11. FIG. 6 shows a modified arrangement of this embodiment wherein the reference electrode 12 is longer than the sensing electrode 11.

Figure 4A:
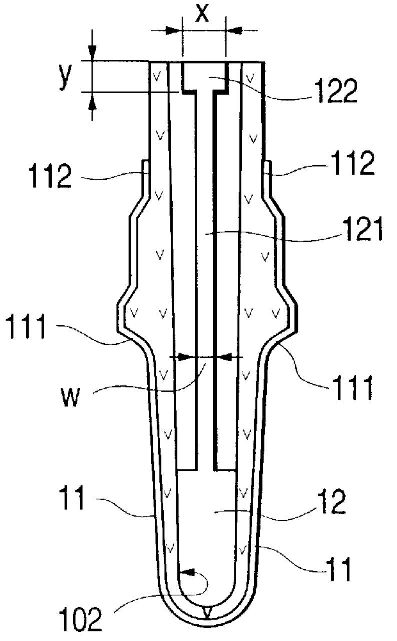
FIG. 4A is a vertical cross-sectional view showing the solid electrolytic body taken along a line A—A shown in FIG. 3.

As shown in FIGS. 1 and 4A, the external lead electrode 111 and the internal lead electrode 121 have a circumferential width W of 1.5 mm. The external and internal terminal electrodes 112 and 122 serves as signal outlet portions for transmitting signals from the external and internal lead electrodes 111 and 121 to the outside. More specifically, the external and internal terminal electrodes 112 and 122 are connected to terminals 681 and 682 of an oxygen sensor 6 which will be explained later in detail.

As shown in FIGS. 1 and 4A, the external terminal electrode 112 and the internal lead electrode 122 are a rectangle having a circumferential width "x (=7 mm)" and an axial length "y (=5 mm)". The width "x" may be identical with that of the external and internal lead electrodes 111 and 121.

Figure 4B:
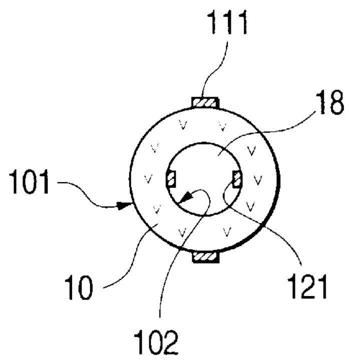
FIG. 4B is a transverse cross-sectional view showing the solid electrolytic body taken along a line B—B shown in FIG. 3.

As shown in FIG. 4B, two external lead electrodes 111 are provided at opposite positions on the outer surface 101, while two internal lead electrodes 121 are provided at opposite positions on the inner surface 102. A total of four lead electrodes 111 and 112 are mutually spaced with angular intervals of 90°.

The heater 19 is made of $Al_2O_3$, $Si_3N_4$ or the like.

As shown in FIG. 2, the heat-generating resistor element 190 has a longitudinal length of 7.0 mm with its lower end spaced from the lower end of the heater 19 by a distance 1.0 mm. A preferable material for the heat-generating resistor element 190 is W-Re, Pt or the like.

The upper end of the heat-generating resistor element 190 is positioned at a level equivalent to the position spaced from the element tip 14 by a distance 0.56L (=10 mm).

The heater 19 comprises a core member and an $Al_2O_3$ ceramic sheet wound around the core. The heat-generating resistor element 190 is disposed at a reverse side of the $Al_2O_3$ ceramic sheet.

It is possible to use a multilayered heater comprising a rectangular $Al_2O_3$ substrate and a coating substrate accumulated thereon.

As shown in FIG. 5, the contact portion 100 includes the inner point "Pi" where the heater 19 is brought into contact with the inner surface 102 of the solid electrolytic body 10 and the outer point "Po" opposing the inner point "A" via the solid electrolytic body 10, together with the neighboring region including the vicinity of these points "Pi" and "Po." The sensing electrode 11 includes the outer point "Po" of the contact portion 100. The inner point "Pi" is positioned at a level higher than the element tip 14 by a distance 0.11L (=2.0 mm).

The sensing electrode 11 is fabricated in the following manner.

A paste is printed on the outer surface 101 of the solid electrolytic body 10 by pad printing, so as to form a printed pattern corresponding to the sensing electrode 11, the external lead electrode 111, and the external terminal electrode 112. This paste contains di-benzylidene platinum with a noble metal amount of 0.4 wt %. Next, the printed paste is heat treated to form a Pt nucleus.

Then, chemical plating is applied on the Pt nucleus to form the electrodes (i.e., sensing electrode 11 and others) each having a thickness of 1 $\mu$m.

According to this embodiment, the external lead electrode 111 and the external terminal electrode 112 are formed simultaneously together with the sensing electrode 11 by the chemical plating. However, the external lead electrode 111 may be a paste electrode.

The reference electrode 12 is fabricated in the following manner.

A dispenser, filled with an organometallic paste containing a noble metal or a paste containing a noble metal, is prepared to insert its nozzle into the reference gas chamber 18. The nozzle is shifted along the inner surface 102 in the up-and-down direction and rotated about an axis to form a printed pattern of the paste corresponding to the reference electrode 12, the internal lead electrode 121 and the internal terminal electrode 122.

When the noble metal containing organometallic paste is applied, the plating is performed after finishing the heat treatment. On the other hand, the noble metallic paste is directly sintered. Thus, the reference electrode 12 is obtained.

It is possible to attach a porous member, like a foam member, to the tip end of the dispenser.

Next, a detailed arrangement of the oxygen sensor 6 equipped with the oxygen sensing element 1 will be explained.

Figure 7:
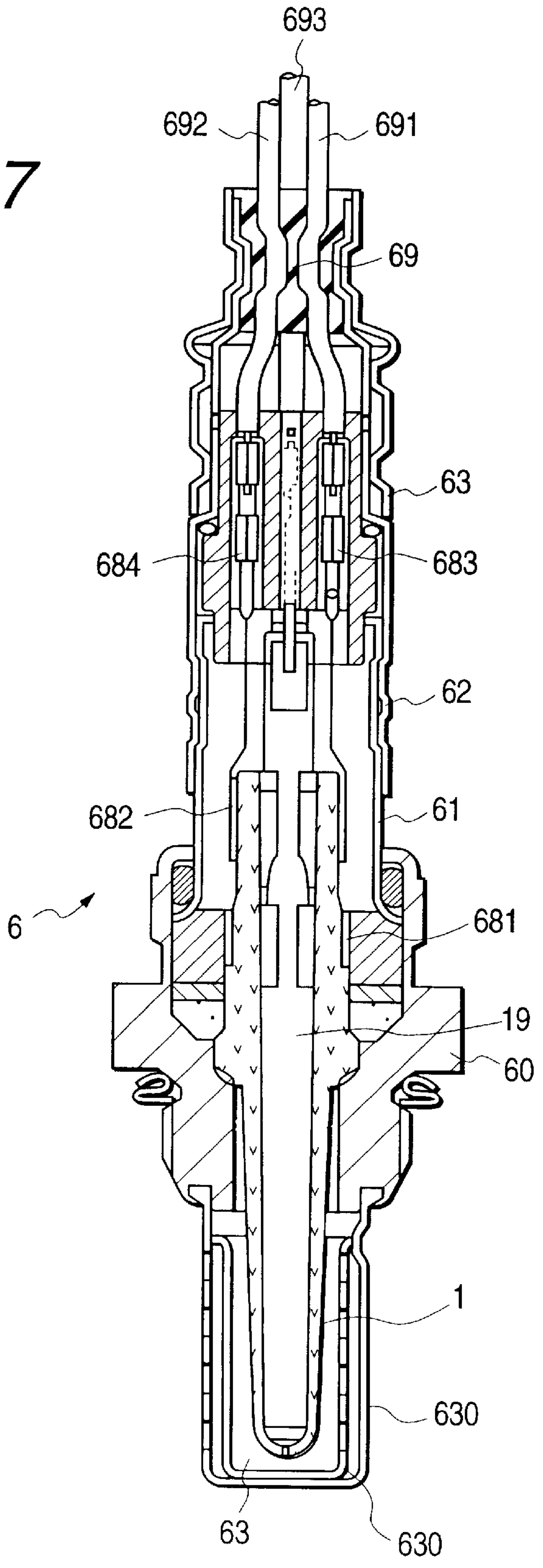
FIG. 7 is a cross-sectional view showing an oxygen sensor in accordance with the first embodiment of the present invention.

As shown in FIG. 7, the oxygen sensor 6 comprises a housing 60 and the oxygen sensing element 1 accommodated in this housing 60. A measuring gas chamber 63 is provided below the housing 60. A double-layered cover 630 surrounds the tip end region of the oxygen sensing element 1. Three-stage covers 61, 62 and 63 are sequentially provided above the housing 60.

The reference gas chamber 18 of the oxygen sensing element 1 accommodates the rod heater 19 with a predetermined clearance between the heater 19 and the inner surface 102.

A plurality of leads 691~693 extend upward through an elastic insulating member 69 provided at the upper end of the covers 62 and 63. The leads 691 and 692 transmit current signals generated from the solid electrolytic body 10 to the outside, while the lead 693 supplies electric power to the heater 19.

The leads 691 and 692 have connecting terminals 683 and 684 at their lower ends. The connecting terminals 683 and 684 are connected to the terminals 681 and 682 fixed on the oxygen sensing element 1.

The terminals 681 and 682 are fixed to the external and internal terminal electrodes 112 and 122 of the oxygen sensing element 1, respectively.

When the oxygen sensor is heated, the temperature of the oxygen sensor increases along a temperature-increase profile. After the temperature is stabilized, the oxygen sensor body has a temperature distribution.

Figure 8:
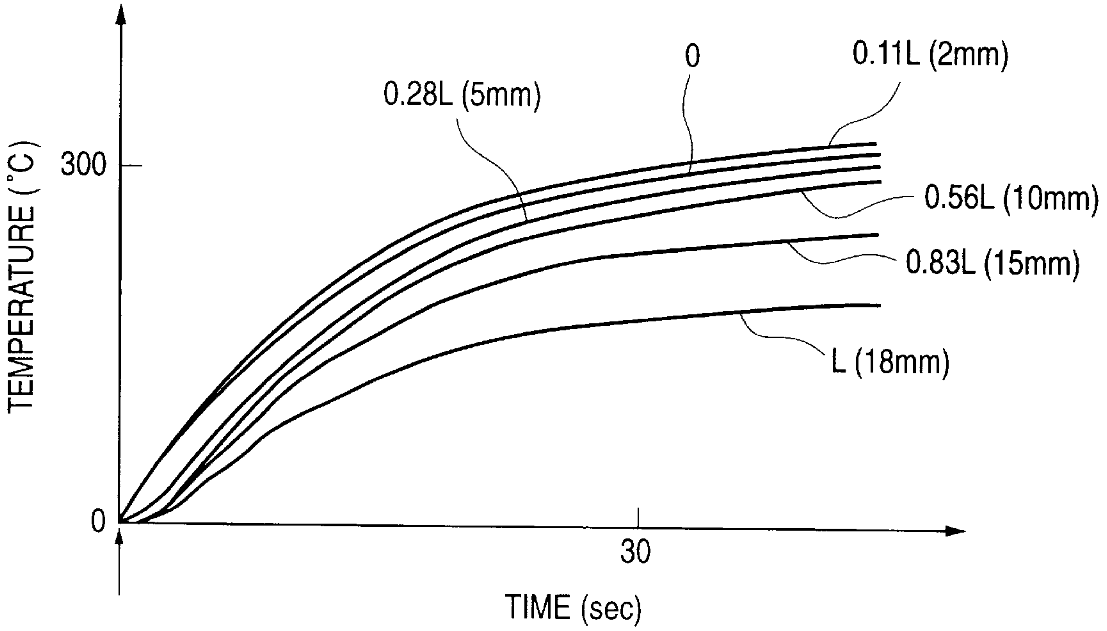
FIG. 8 is a graph showing the profile of temperature increase of the oxygen sensing element in accordance with the first embodiment of the present invention.

The inventors experimentally measured the temperature-increase profile and the temperature distribution. The oxygen sensing element 1 is exposed to the measuring gas of 400° C. to measure temperature increases at a plurality of sampling points through thermocouples, while the sensor output is monitored. FIG. 8 shows the result of measurement.

In FIG. 8, curve "0" represents a temperature-increase profile at the element tip 14, curve "0.11L" represents a temperature-increase profile at the contact portion 100, curve "0.56L" represents a temperature-increase profile at a point "k" shown in FIG. 1 corresponding to the upper end of the sensing electrode 11, curve "0.83L" represents a temperature-increase profile at a position spaced 15 mm away from the element tip 14, and curve "L" represents a temperature-increase profile at a point "h" shown in FIG. 1 corresponding to the upper end of the gas receiving surface region 13.

Figure 9:
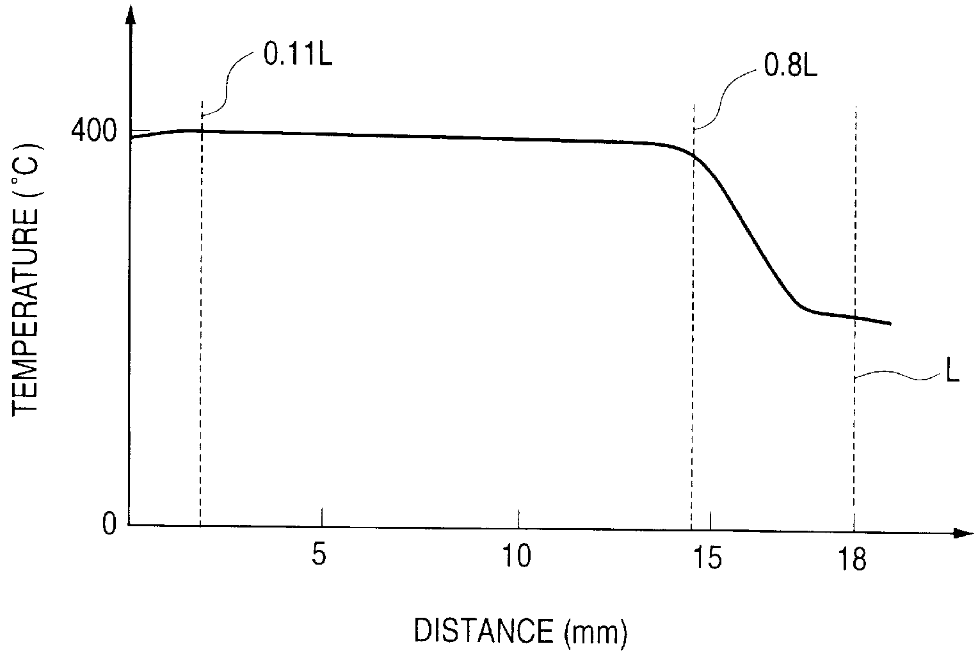
FIG. 9 is a graph showing a temperature distribution of the oxygen sensing element measured after the temperature is stabilized.

Then, after the temperature of the oxygen sensing element 1 is stabilized at 400° C., a temperature distribution is obtained by measuring temperatures at the sampling points sequentially arranged along the gas receiving surface region 13 from the distal end (origin; 0 mm). FIG. 9 shows the result of measurement.

As shown in FIG. 8, the fastest temperature increase occurs at the contact portion 100 where the heater 19 is brought into contact with the inside surface 102 of the oxygen sensing element 1. The temperature increase at the element tip 14 follows this. On the contrary, it takes a long time to increase the temperature at the upper end of the gas receiving surface region 13. Furthermore, the speed of temperature increase suddenly decreases when the distance of the sampling point from the element tip 14 exceeds 0.8L.

As shown in FIG. 9, the temperature distribution of the oxygen sensing element 1 is uniform in the range from the element tip 14 to the 0.8L position but steeply declines in the region exceeds 0.8L.

The oxygen sensing element of the present invention functions in the following manner.

The inner surface 102 of the oxygen sensing element 1 is brought into contact with the heater 19 at the contact portion 100. The sensing electrode 11 includes at least part of the contact portion 100.

Heat generated from the heater 19 is directly transmitted to the sensing electrode 11 via the inner surface 102 and the solid electrolytic body 10. Thus, the sensing electrode 11 is directly heated by the heater 19. Accordingly, the present invention reduces the activation time required from initiation of heating by the heater 19 to generation of an accurate sensor signal from the activated sensing element 1.

The contact portion 100 is located in the region extending from the element tip 14 to the position spaced by the distance 0.4L away from the element tip 14. With this arrangement, it becomes possible to reduce the heat leakage toward the upper low-temperature region of the oxygen sensing element 1. Thus, the heating efficiency of the heater 19 is improved.

The sensing electrode 11 is entirely located in the region extending from the element tip 14 to the position spaced by the distance 0.8L away from the element tip 14. Thus, the sensing electrode 11 can maintain a high temperature during operation of the sensing element 1 (refer to FIG. 8), realizing uniform temperature distribution and satisfactory response. The activation time is shortened.

Thus, the present invention provides an oxygen sensing element rapid in activation and excellent in response.

The oxygen sensing element 1 can be coated by various layers.

Figure 10:
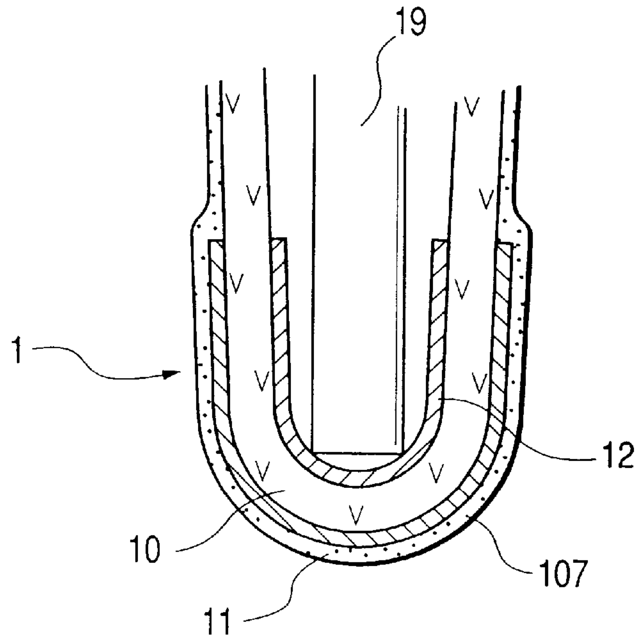
FIG. 10 is a cross-sectional view showing an essential arrangement of a modified oxygen sensing element with a protecting layer in accordance with the first embodiment of the present invention.

FIG. 10 shows a modified oxygen sensing element 1 having a protecting layer 107 of $MgAl_2O_4$ spinel formed by plasma spray. The protecting layer 107 has a thickness of 100 $\mu$m and a porous rate of 20%. The protecting layer 107 also functions as a diffusion resistive layer. According to this arrangement, the protecting layer 107 is formed on an entire surface of the gas receiving surface region 13 of the oxygen sensing element 1. However, even when the protecting layer 107 is small, the similar effects will be obtained when the protecting layer 107 can completely cover the sensing electrode 11.

The protecting layer 107 prevents the thermal shrinking of electrodes.

Figure 11:
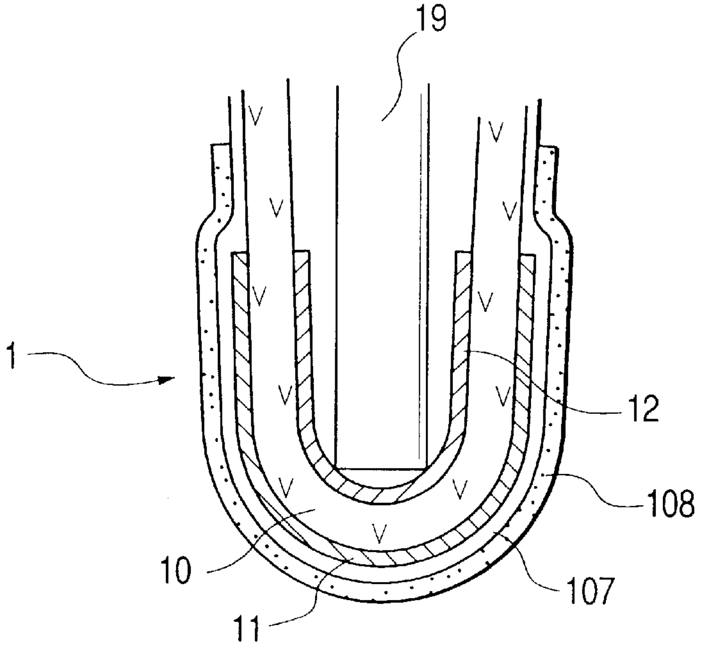
FIG. 11 is a cross-sectional view showing an essential arrangement of a modified oxygen sensing element with two protecting layers in accordance with the first embodiment of the present invention.

FIG. 11 shows another modified oxygen sensing element 1 having a second protecting layer 108 formed on the surface of the protecting surface 107. The second protecting layer 108 traps poisonous components in the measuring gas and chiefly contains $Al_2O_3$. The second protecting layer 108 has a thickness of 120 μm and a pore rate of 20~50%.

A fabrication method of the second protecting layer 108 will be explained.

For example, the oxygen sensing element 1 with the protecting layer 107 is dipped into a slurry of $Al_2O_3$ and then heat treated to form the second protecting layer 108.

Effect of the second protecting layer 108 is sufficiently obtained when the sensing electrode 11 is covered by the second protecting layer 108. According to this arrangement, the second protecting layer 108 extends from the element tip 14 to a position spaced by a distance of 12 mm (=0.67L) away from the element tip 14. However, it is possible to enlarge the second protecting layer 108 along the entire surface of the gas receiving surface region 13.

Figure 12:
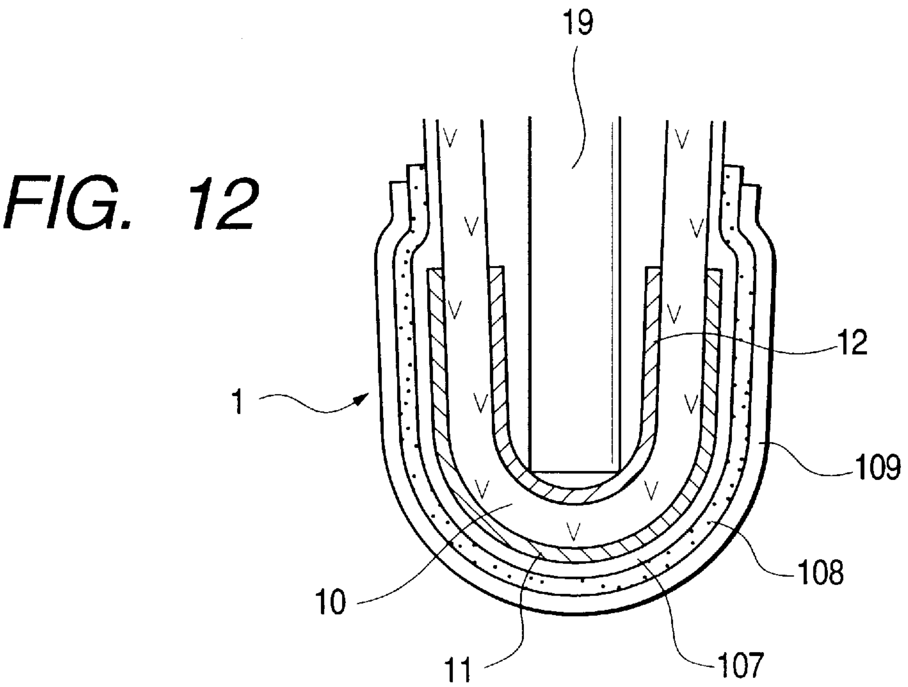
FIG. 12 is a cross-sectional view showing an essential arrangement of a modified oxygen sensing element with three protecting layers in accordance with the first embodiment of the present invention.

FIG. 12 shows another modified oxygen sensing element 1 having a third protecting layer 109 formed on the surface of the second protecting layer 108 formed on the surface of the protecting surface 107. The third protecting layer 109 enhances the effect of the protecting layers trapping the poisonous components in the measuring gas.

When the third protecting layer 109 has a porous rate larger than that of the second protecting layer 108, it becomes possible to trap large poisonous components. This is effective to prevent the second protecting layer 108 from being blinded by poisonous members. The third protecting layer 109 chiefly contains $Al_2O_3$ and has a thickness of 40μm and a pore rate of 60%.

A fabrication method of the third protecting layer 109 will be explained.

For example, the oxygen sensing element 1 with the second protecting layer 108 is dipped into a slurry of $Al_2O_3$ and then heat treated to form the third protecting layer 109.

Effect of the third protecting layer 109 is sufficiently obtained when the sensing electrode 11 is covered by the third protecting layer 109. According to this arrangement, the third protecting layer 109 extends from the element tip 14 to a position spaced by a distance of 11 mm (=0.61L) away from the element tip 14.

Tables 1 and 2 show experimental data obtained from the performance tests of samples 1~16 of the oxygen sensing element. The samples 1~9 are substantially the same in their arrangement as the oxygen sensing element 1 disclosed in the first embodiment of the present invention, although slightly different in size, positional relationship, and fabrication method for the sensing electrode.

Each of the samples 1~15 has a reference electrode provided entirely on the inner surface of the oxygen sensing element. Each of the samples 1–9 and 16 has reference and sensing electrodes provided in an opposed relationship. In each sample, the external and internal lead electrodes are formed in the 90-degree offset arrangement shown in FIG. 4B.

In respective Tables 1 and 2, the "sensing electrode position" represents a distance between the lower end of the sensing electrode and the distal end of the oxygen sensing element. The "contact position" represents a distance between the contact portion and the distal end of the oxygen sensing element. The "external lead electrode width" represents a circumferential length of the external lead electrode as explained in the foregoing description.

Figure 16A:
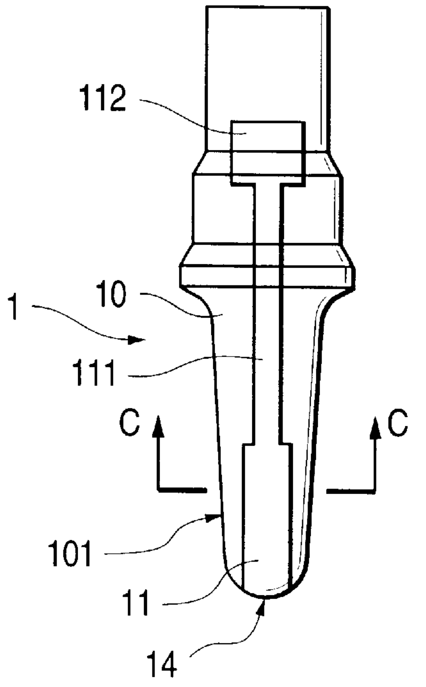
FIG. 16A is a side view showing another oxygen sensing element with a sensing electrode partly formed in the circumferential direction in accordance with the first embodiment of the present invention.
Figure 16B:
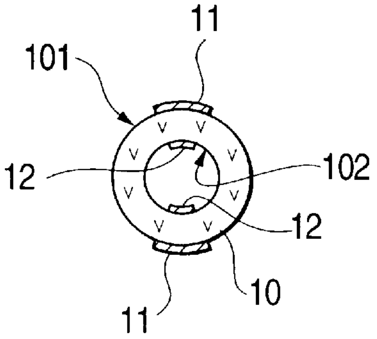
FIG. 16B is a transverse cross-sectional view taken along a line C—C of FIG. 16A.

The sample 8 has a partly formed external electrode (its circumferential width is 3 mm) according to a modified arrangement shown in FIGS. 16A and 16B.

The performance tests, including measurements of activation time, sensor response (sensor output, response time), and durability, will be explained in more detail.

First, measurement of the activation time is explained.

The oxygen sensing element samples were exposed to the measuring gas of rich (λ[air excessive rate]=0.9) and 400° C. At the same time, electric power was supplied to the heater. A time required for the sensor to produce a 0.45 V output signal is defined as an activation time. Every ○-marked sample demonstrated an acceptable activation time equal to or less than 30 seconds.

Second, measurement of the response is explained.

Each of the oxygen sensing element samples, maintained at 400° C., was alternately subjected to rich measuring gas (λ=0.9) and lean measuring gas (λ=1.1) to check the output signal response about a reference level of 0.45 V. Every ○-marked sample demonstrated satisfactory response in the sensor output frequency which is equal to or larger than 0.8 Hz as well as in the sensor output difference which is equal to or larger than 0.7 V as a difference between a sensor output corresponding to the rich measuring gas (λ=0.9) and a sensor output corresponding to the lean measuring gas (λ=1.1).

Next, measurement of the durability is explained. The oxygen sensing element samples were left in a high-temperature environment of 900° C. for 500 hours. Every ○-marked sample demonstrated good durability equivalent to or larger than 0.4 Hz in the sensor output frequency and 0.5 V in the sensor output difference.

All of the samples 1~9 shown in Table 1 satisfy the condition that the contact portion is positioned in the region from the distal end of the oxygen sensing element to the 0.4L position and the sensing electrode is positioned in the region from the distal end to the 0.8L position. The samples 1~9 demonstrated short activation time, excellent response and higher output.

The sample 10, having a sensing electrode positioned higher than 0.8L, was insufficient in the response. The sample, having a contact portion formed at a higher position, was insufficient in the activation time. The sample 12, having a wide external lead electrode, was insufficient in the response. The sample 13, having a narrow external lead electrode, was insufficient in the durability.

The sample 14, having a sensing electrode fabricated by paste printing, was insufficient in the activation time, in the response, and in the sensor output response. The sample 15, having a sensing electrode not formed in the contact portion, was insufficient in the activation time.

According to Tables 1 and 2, it was confirmed that it becomes possible to provide an oxygen sensing element having a short activation time, excellent response, and a higher output when the contact portion is positioned in the region from the 0 (or 0L) position (i.e., the distal end of the oxygen sensing element) to the 0.4L position and the sensing electrode is positioned in the region from the 0 position to the 0.8L position.

It is also confirmed that it is preferable to fabricate the sensing electrode by chemical plating. A preferable width of the external lead electrode is in the range of 0.1~5 mm.

The sample 9 differs from the sample 1 in the condition of the reference electrode. According to the sample 9, the sensing electrode and the sensing electrode are disposed in an opposed relationship. The sample 9 is slightly excellent than the sample 1 in the response and the sensor output.

TABLE 1

| sample No. | 1 | 2 | 3 | 4 | 5 | 6 | 7 | 8 | 9 |
|---|---|---|---|---|---|---|---|---|---|
| sensing electrode position (mm) | 0 | ← | ← | ← | ← | ← | 2 (0.11L) | 0 | 0 |
| sensing electrode length (mm) | 10 (0.56L) | 14 (0.78L) | 2 (0.11L) | 10 (0.56L) | ← | ← | 8 (0.44L) | 10 (0.56L) | ← |
| contact position (mm) | 2 (0.11L) | ← | ← | 6 (0.33L) | 2 (0.11L) | ← | ← | ← | ← |
| external lead electrode width (mm) | 1.5 | ← | ← | ← | 0.1 | 5.0 | 1.5 | ← | ← |
| fabrication method | chemical plating | ← | ← | ← | ← | ← | ← | ← | ← |
| activation time (sec) | 20 ○ | 21 ○ | 20 ○ | 23 ○ | 21 ○ | 22 ○ | 25 ○ | 24 ○ | 20 ○ |
| response frequency (Hz) | 0.88 ○ | 0.86 ○ | 0.85 ○ | 0.86 ○ | 0.85 ○ | 0.82 ○ | 0.92 ○ | 0.81 ○ | 0.9 ○ |
| sensor output (V) | 0.77 ○ | 0.73 ○ | 0.75 ○ | 0.75 ○ | 0.80 ○ | 0.73 ○ | 0.80 ○ | 0.73 ○ | 0.8 ○ |
| durability | ○ | ○ | ○ | ○ | ○ | ○ | ○ | ○ | ○ |

TABLE 2

| sample No. | 10 | 11 | 12 | 13 | 14 | 15 | 16 |
|---|---|---|---|---|---|---|---|
| sensing electrode position (mm) | 0 | ← | ← | ← | ← | 4 (0.22L) | 0 |
| sensing electrode length (mm) | 15 (0.83L) | 10 (0.56L) | ← | ← | ← | 8 (0.44L) | 15 (0.83L) |
| contact position (mm) | 2 (0.11L) | 8 (0.44L) | 2 (0.11L) | ← | ← | ← | ← |
| external lead electrode width (mm) | 1.5 | ← | 6 | 0.08 | 1.5 | 1.5 | 1.5 |
| fabrication method | chemical plating | ← | ← | ← | paste printing | chemical plating | ← |
| activation time (sec) | 28 ○ | 38 x | 26 ○ | 21 ○ | 42 x | 34 x | 28 ○ |
| response frequency (Hz) | 0.78 x | 0.85 ○ | 0.75 x | 0.90 ○ | 0.65 x | 0.90 ○ | 0.79 x |
| sensor output (V) | 0.66 x | 0.71 ○ | 0.67 x | 0.80 ○ | 0.56 x | 0.77 ○ | 0.68 x |
| durability | ○ | ○ | ○ | x | ○ | ○ | ○ |

FIGS. 13 through 18 show various modifications of the oxygen sensing element 1 in accordance with the present invention.

Figure 13:
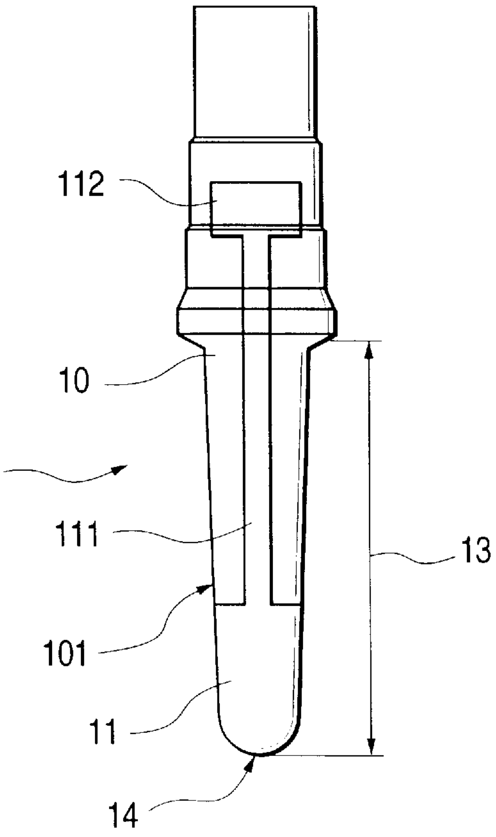
FIG. 13 is a side view showing another oxygen sensing element with an elongated gas receiving surface region in accordance with the first embodiment of the present invention.

FIG. 13 shows a modified oxygen sensing element 1 having the gas receiving surface region 13 which is 25 mm in length. The sensing electrode 11 extends from the element tip 14 to the 0.4L (=10 mm) position. The external lead electrode 111 is 1.5 mm in width. The external terminal electrode 112 is a rectangular electrode (7 mm in width×4 mm in length). The rest is substantially the same as the arrangement disclosed in the above-described embodiment.

Figure 14:
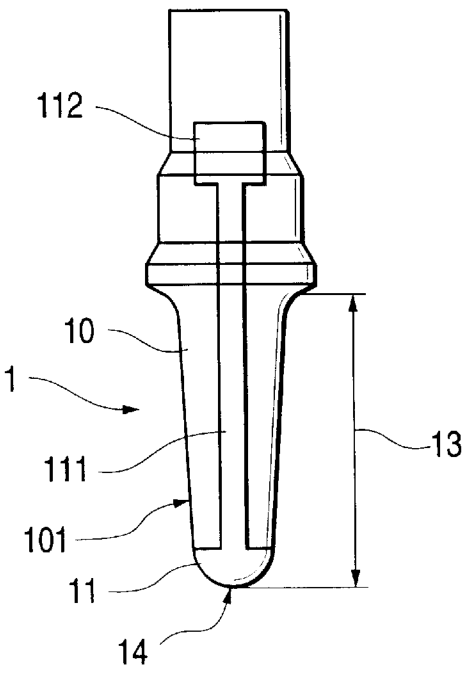
FIG. 14 is a side view showing another oxygen sensing element with a short sensing electrode in accordance with the first embodiment of the present invention.

FIG. 14 shows another modified oxygen sensing element 1 having the sensing electrode 11 extending from the element tip 14 to the 0.11 (=2 mm) position. The external lead electrode 111 and the external terminal electrode 112 are identical with those of the above-described embodiment. The modified oxygen sensing element 1 of FIG. 14 corresponds to the sample 3 shown in Table 1 and, therefore, has a short activation time, excellent response, and a higher output.

Furthermore, the sensing electrode 11 has a smaller area. This is effective to reduce the used amount of Pt which is expensive. Thus, the manufacturing cost is reduced. The rest is substantially the same as the arrangement disclosed in the above-described embodiment.

Figure 15:
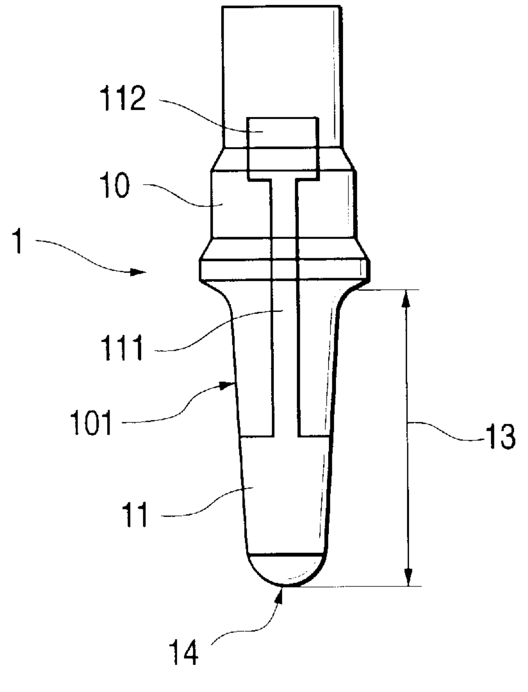
FIG. 15 is a side view showing another oxygen sensing element with a sensing electrode not formed at the distal end in accordance with the first embodiment of the present invention.

FIG. 15 shows another modified oxygen sensing element 1 having the sensing electrode 11 extending from the 0.11 (=2 mm) position to the 0.56L (=10 mm) position. The modified oxygen sensing element 1 of FIG. 15 corresponds to the sample 7 shown in Table 1 and, therefore, has a short activation time, excellent response, and a higher output. The rest is substantially the same as the arrangement disclosed in the above-described embodiment.

FIGS. 16A and 16B cooperatively show another modified oxygen sensing element 1 having the sensing electrode 11 extending from the element tip 14 to the 0.56L(=10 mm) position with a circumferential width of 3 mm. A total of two sensing electrodes 11 are provided on the outer surface 101 in an opposed relationship as shown in FIG. 16B. Respective external electrodes 11 oppose to the corresponding reference electrodes 12 formed on the inner surface 102. The modified oxygen sensing element 1 of FIGS. 16A and 16B corresponds to the sample 8 shown in Table 1.

Therefore, the modified oxygen sensing element 1 of FIGS. 16A and 16B has a short activation time, excellent response, and a higher output. Furthermore, the sensing electrode 11 has a smaller area. This is effective to reduce the used amount of an expensive electrode material including noble metal. Thus, the manufacturing cost is reduced.

According to the oxygen sensing element 1 of FIGS. 16A and 16B, the sensing electrode 11 is wider than the external lead electrode 111. It is, however, possible to equalize the widths of them. It is also possible to equalize the widths of the external terminal electrode 112, the external lead electrode 111, and the sensing electrode 11.

Figure 17:
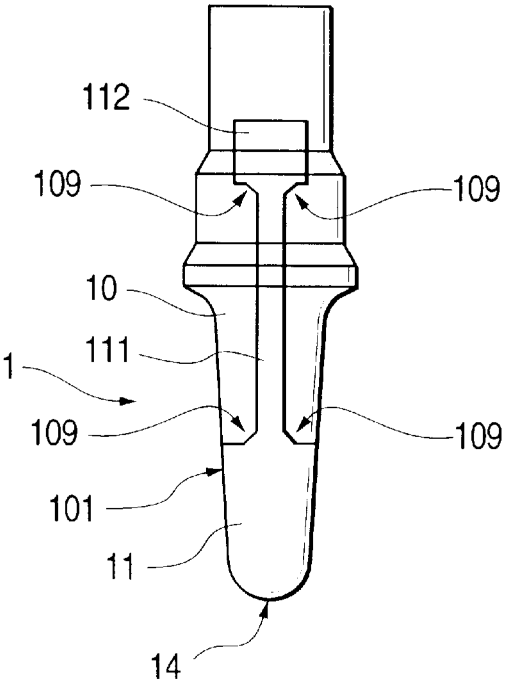
FIG. 17 is a side view showing another oxygen sensing element with tapered portions at the connecting portions between the electrodes formed on the outer surface of the solid electrolytic body in accordance with the first embodiment of the present invention.

FIG. 17 shows another modified oxygen sensing element 1 having tapered portions 109 of 1 mm formed at the connecting portion between the sensing electrode 11 and the external lead electrode 111 and at the connecting portion between the external lead electrode 111 and the external terminal electrode 112. It is possible to provide arc-shaped tapered portions 109. When the electrodes are fabricated by chemical plating and sintering, the connecting portions of the electrodes are subjected to concentrated stresses. Providing the tapered portions 109 is effective to reduce such concentration of stresses, thereby eliminating the breaking of the electrodes at their connecting portions.

Figure 18:
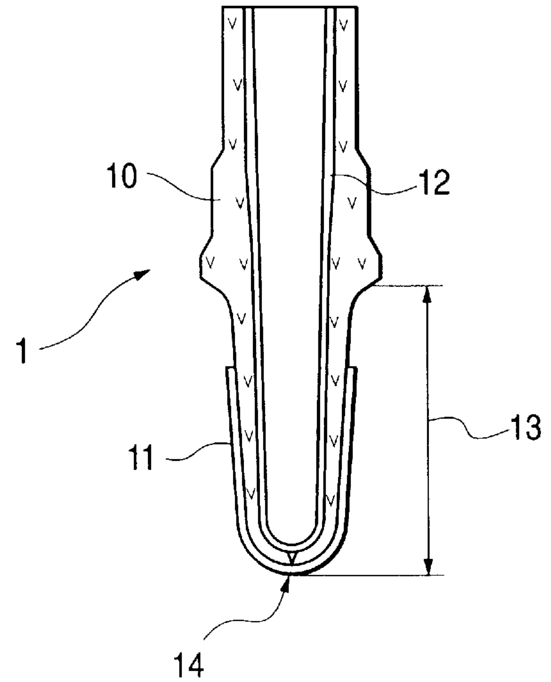
FIG. 18 is a vertical cross-sectional view another oxygen sensing element in accordance with the first embodiment of the present invention, wherein a reference electrode is entirely formed on the inner surface of a solid electrolytic body.

FIG. 18 shows another modified oxygen sensing element 1 having the reference electrode 12 formed on the entire surface of the inner surface of the solid electrolytic body 10.

The reference electrode 12 is formed by dipping the inner surface into an organometallic solution containing a noble metal and then applying the plating after finishing the heat treatment. This is advantageous in that the reference electrode can be easily formed without using a complicated apparatus, such as a dispenser or the like.

The rest is substantially the same as the arrangement disclosed in the above-described embodiment.

Second Embodiment

Figure 20A:
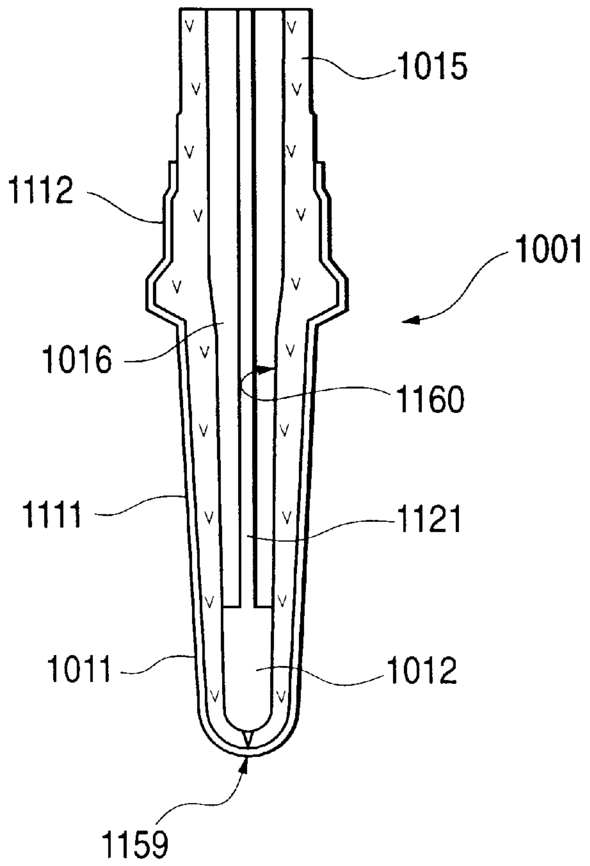
FIG. 20A is a vertical cross-sectional view showing the oxygen sensing element comprising the solid electrolytic body, the sensing electrode and a reference electrode, taken along a line D—D shown in FIG. 19.
Figure 20B:
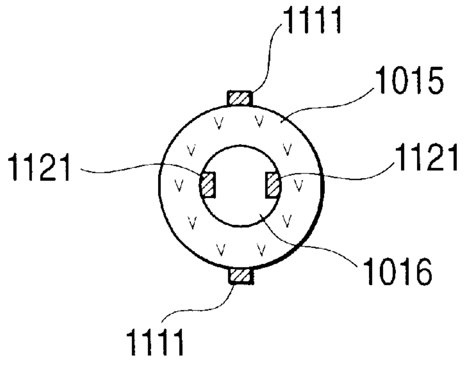
FIG. 20B is a transverse cross-sectional view showing the solid electrolytic body, the sensing electrode and the reference electrode taken along a line E—E shown in FIG. 19.
Figure 21:
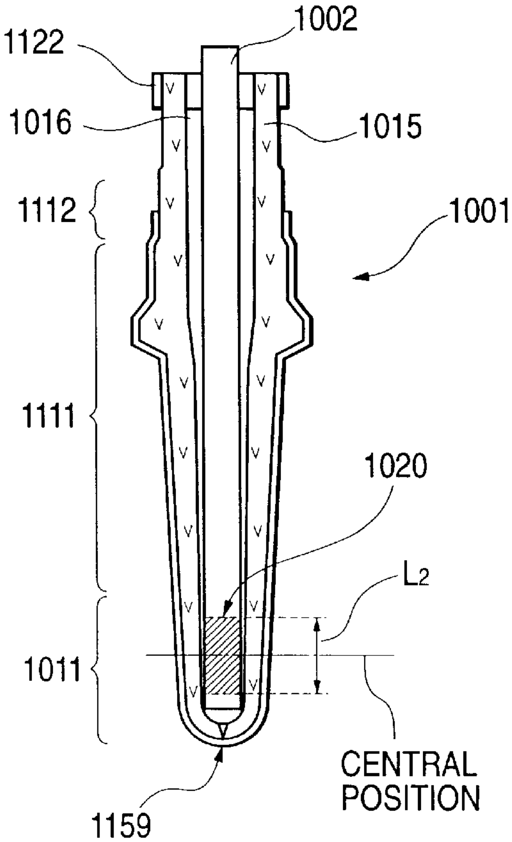
FIG. 21 is a vertical cross-sectional view showing a positional relationship between a heater and the solid electrolytic body of the oxygen sensing element in accordance with the second embodiment of the present invention.

As shown in FIGS. 19 through 23, an oxygen sensing element 1001 of the second embodiment comprises a cup-shaped solid electrolytic body 1015 having one end closed and an inside space serving as a reference gas chamber 1016, a sensing electrode 1011 provided on an outer surface 1150 of the solid electrolytic body 1015, a reference electrode 1012 provided on an inner surface 1160 of the solid electrolytic body 1015, and a heater 1002 disposed in the reference gas chamber 1016 (refer to FIG. 21).

Figure 19:
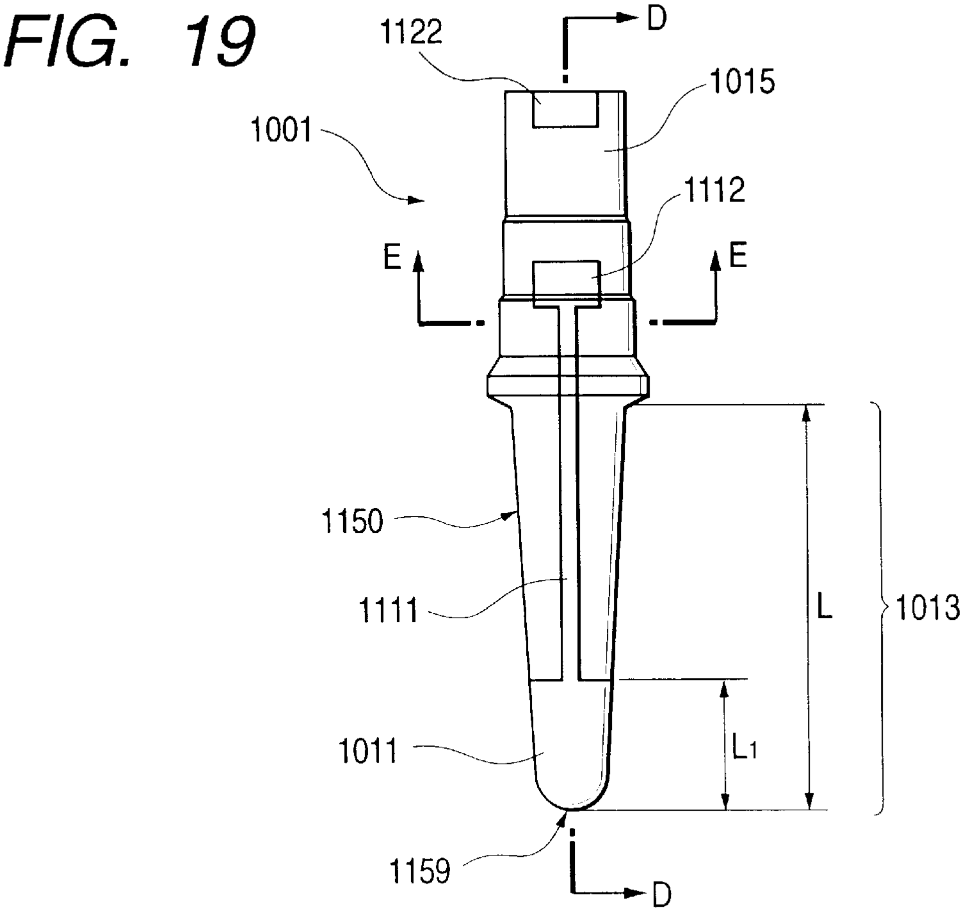
FIG. 19 is a side view showing an oxygen sensing element comprising a solid electrolytic body and a sensing electrode in accordance with a second embodiment of the present invention.

As shown in FIGS. 19, 20A and 20B, the solid electrolytic body 1015 has an outer surface 1150 including a gas receiving surface region 1013 exposed to the measuring gas when the oxygen sensing element 1001 is operated. The gas receiving surface region 1013 extends from an element tip 1159 (i.e., distal end of the oxygen sensing element 1001) to a position spaced by a distance L from the element tip 1159.

The sensing electrode 1011 has a length L1 equal to or larger than 0.2L in the longitudinal direction of the oxygen sensing element 1001. The sensing electrode 1011 is located in a region extending from the element tip 1159 to a position spaced by a distance 0.8L away from the element tip 1159. Furthermore, the sensing electrode 1011 has a thickness of 0.5~3.0 $\mu$m.

Figure 22:
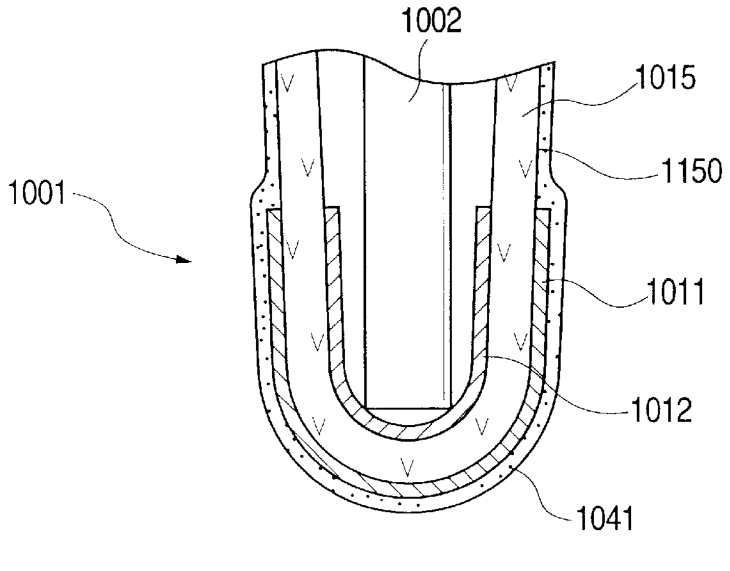
FIG. 22 is an enlarged vertical cross-sectional view showing a protecting layer in accordance with the second embodiment of the present invention.

The oxygen sensing element 1001 has a protecting layer 1041 of $MgAl_2O_4$ spinel formed by plasma spray. As shown in FIG. 22 (although not shown in FIG. 19), the protecting layer 1041 extends on the entire surface of the sensing electrode 1011 and the outer surface 1150.

The protecting layer 1041 has a thickness of 100 $\mu$m and a porous rate of 20%, although the thickness and the porous rate can be varied by adjusting the conditions of the plasma spray.

The protecting layer 1041 protects the sensing electrode 1011 and prevents the sensing electrode 1011 from shrinking by heat. The protecting layer 1041 also functions as a diffusion resistive layer. It is possible to provide the protecting layer 1041 only on the surface of the sensing electrode 1011.

As shown in FIG. 19, a lead portion 1111 extends on the outer surface 1150 of the solid electrolytic element 1015 to transmit a sensing signal from the sensing electrode 1011 to a terminal portion 1112. Although not shown in FIG. 19, a total of two lead portions 1111 are provided on the outer surface of the solid electrolytic body in an opposed relationship and a total of two and two lead electrode 1121 are provided in the same manner (refer to FIGS. 20A and 20B).

The solid electrolytic body 1015 is made of a partially stabilized zirconia. All of the sensing electrode 1011, the lead portion 1111 and the terminal portion 1112 are made of platinum.

The length L of the gas receiving surface region 1013 is 25 mm.

The sensing electrode 1011 and the reference electrode 1012 cooperatively detect the oxygen concentration of the measuring gas. The sensing electrode 1011 extends from the element tip 1159 to a position spaced by an altitudinal distance of 10 mm away from the element tip 1159. In other words, the length L1 of the sensing electrode 1011 is 10 mm (i.e., 0.40L).

The lead portion 1111, transmitting the sensing signal from the sensing electrode 1011 to the terminal portion 1112, has a circumferential width of 1.5 m and is connected between the upper end of the sensing electrode 1011 and the lower end of the terminal portion 1112.

Figure 23:
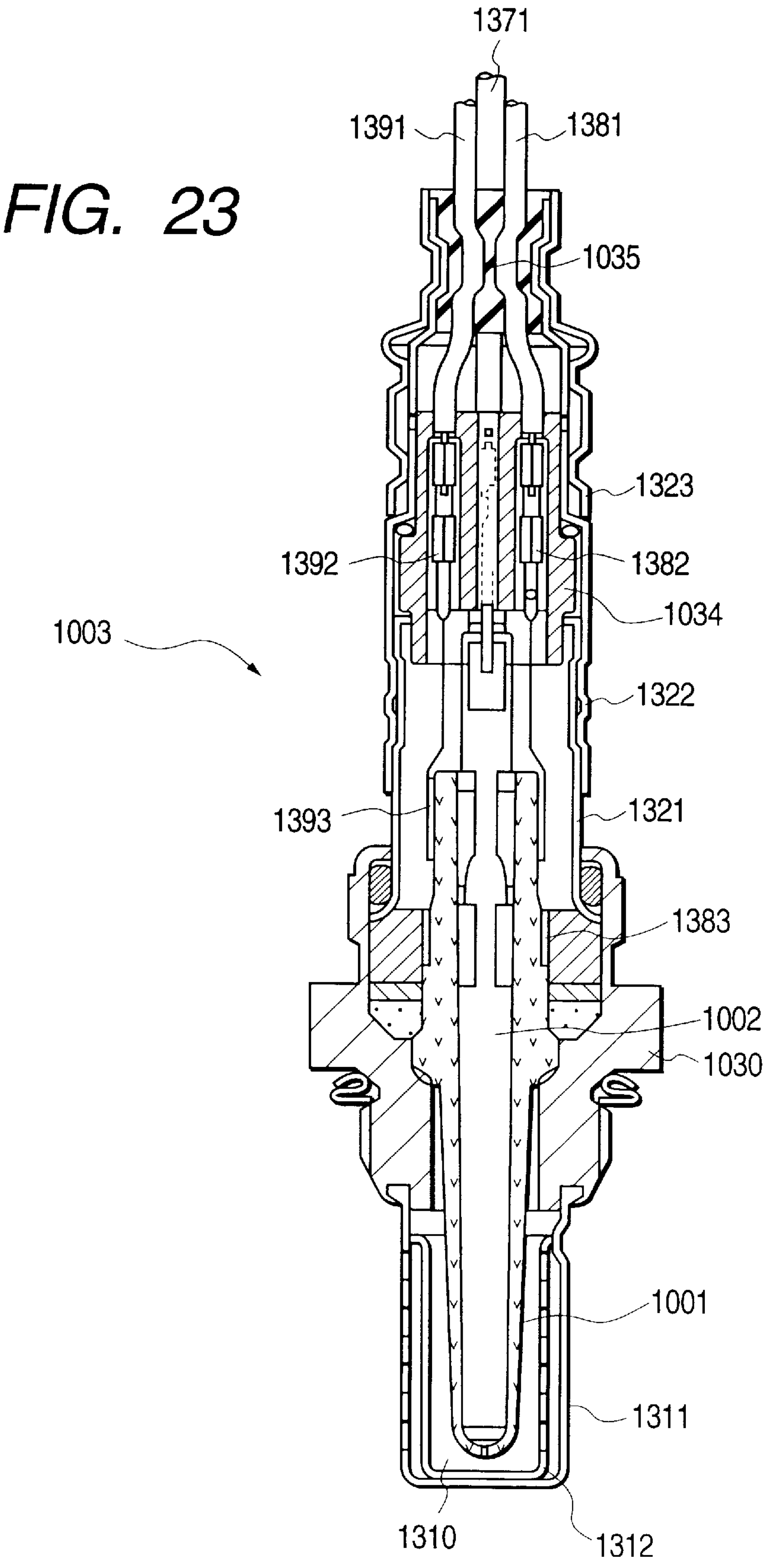
FIG. 23 is a vertical cross-sectional view showing an overall arrangement of an oxygen sensor having the oxygen sensing element in accordance with the second embodiment of the present invention.

The terminal portion 1112 is connected to a metallic terminal 1383 of the oxygen sensor 1003 to transmit the sensing signal to the outside as shown in FIG. 23. The terminal portion 1112 is a rectangle having a circumferential width of 7 mm and a longitudinal length of 5 mm. It is possible to equalize the circumferential width of the terminal portion 1112 with that of the lead portion 1111.

As shown in FIGS. 20A and 20B, two lead portions 1111 are paired so as to oppose via the solid electrolytic body 1015 and two terminal portions 1112 are paired in the same manner.

The reference electrode 1012 is fabricated by plating, paste printing or the like at a position opposed to the sensing electrode 1011. A lead portion 1121 extends on the inner surface 1160 to transmit a reference signal from the reference electrode 1012 to a terminal portion 1122.

The lead portion 1121 has a circumferential width of 1.5 mm. The terminal portion 1122 is a rectangle having a circumferential width of 7 mm and a longitudinal length of 5 mm. Two lead portions 1121 and two lead portions 1111 are offset with angular intervals of 90°.

With this arrangement, it becomes possible to eliminate adverse influence from the low-temperature portions of the lead portions 1121 and 1111. The sensor response can be improved. However, it may be possible to dispose the lead portions 1121 and 1111 in an opposed relationship when no adverse influence is given to the sensor characteristics.

The oxygen sensing element 1001 comprises the heater 1002 which has a heat generating portion 1020 at one end thereof as shown in FIG. 21. The heater 1002 accommodates a resistor element generating heat in response to supplied electric power and leads supplying electric power to this resistor element. The heat generating portion 1020 is a portion where the resistor element is disposed. The heater 1002 chiefly generates heat from the heat generating portion 1020.

The heater 1002 has a main body of $Al_2O_3$, $Si_3N_4$ or the like which accommodates the resistor element of W-Re, Pt or the like.

The heater 1002 comprises a heater sheet wound around a heater core of $Al_2O_3$, $Si_3N_4$ or the like. The heat-generating resistor element is provided on a surface of the heater sheet so as to face the heater core, or provided in the layered body of the heater sheet.

It is possible to use a multilayered heater comprising a plurality of platelike $Al_2O_3$ layers.

The heat generating portion 1020 has a lower end corresponding to an altitudinal distance 1.0 mm from the element tip 1159 and extends upward with a length L2=4.0 mm (i.e., 0.16L). The central position of the heat generating portion 1020 corresponds to an altitudinal distance 5 mm from the element tip 1159. A clearance of 0.2 mm is provided between the inner surface 1160 and the heater 1002 at a level of the sensing electrode 1011.

According to this embodiment, the heater 1002 is brought into contact with the inner surface 1160 of the reference gas chamber 1016. However, it is possible to dispose the heater 1002 in a separated relationship to the inner surface 1160.

The sensing electrode 1011, the lead portion 1111, and the terminal portion 1112 are fabricated in the following manner.

A paste containing a noble metallic compound, such as di-benzylidene platinum (with a Pt amount of 0.4 wt %), is printed on the outer surface 1150 of the solid electrolytic body 1015 by pad printing, so as to form a printed pattern corresponding to the sensing electrode 1011, the lead portion 1111, and the terminal portion 1112. Next, the printed paste is heat treated to form a Pt nucleus.

Then, electroless plating is applied on the Pt nucleus to form the sensing electrode 1011, the lead portion 1111, and the terminal portion 1112 each having a thickness of 1.5 $\mu$m.

The reference electrode 1012, the lead portion 1121, and the terminal portion 1122 are fabricated in the following manner. An empty, nozzle equipped dispenser is prepared. The nozzle has a simple outlet opening. It is, however, possible to attach a porous member, like a foam member, to the tip end of the nozzle.

The nozzle of the dispenser is inserted into the reference gas chamber 1016 of the solid electrolytic body 1015. An organometallic paste containing a noble metal or any other paste containing a noble metal is injected into the dispenser. The nozzle is shifted along the inner surface 1160 in the up-and-down direction and rotated about an axis to form a printed pattern of the paste corresponding to the reference electrode 1012, the lead portion 1121, and the terminal portion 1122.

When the noble metal containing organometallic paste is applied to obtain the reference electrode 1012 and others, the chemical plating is performed after finishing the heat treatment. On the other hand, the noble metallic paste is applied, the applied paste is directly sintered to obtain the reference electrode 1012 and others.

Next, a detailed arrangement of the oxygen sensor 1003 comprising the oxygen sensing element 1001 will be explained.

As shown in FIG. 23, the oxygen sensor 1003 comprises a housing 1030 and the oxygen sensing element 1001 sealed and firmly fixed in this housing 1030. The heater 1002 is disposed in the reference gas chamber 1016 of the oxygen sensing element 1001.

A measuring gas chamber 1310 is provided below the housing 1030. A double-layered covers 1311 and 1312 surround the tip end region of the oxygen sensing element 1001. Three-stage covers 1321, 1322 and 1323 are sequentially provided above the housing 1030.

The measuring gas flows into the measuring gas chamber 1310. The air is introduced into an inside space of the covers 1321, 1322 and 1323. The oxygen sensing element 1001, airtightly sealed and fixed in the oxygen sensor body, serves as a partition for separating the air and the measuring gas.

A plurality of leads 1371, 1381 and 1391 extend upward through an elastic insulating member 1035 provided at the upper end of the covers 1322 and 1323. The leads 1381 and 1391 transmit the signals generated from the oxygen sensing element 1001 to the outside, while the lead 1371 supplies electric power to the heater 1002.

The leads 1391 and 1381 have connecting terminals 1382 and 1392 at their lower ends. The connecting terminals 1382 and 1392 are connected to the metallic terminals 1383 and 1393 fixed on the oxygen sensing element 1001.

The metallic terminals 1383 and 1393 are fixed to the terminal portions 1112 and 1122 of the oxygen sensing element 1001, respectively.

According to the oxygen sensing element 1001 of this embodiment, the length L1 of the sensing electrode 1011 is equal to or larger than 0.2L. This arrangement prevents undesirable thermal shrinkage of the sensing electrode 1011 and accordingly prevents the breaking of the sensing electrode 1011 (refer to later described experimental data).

The sensing electrode 1011 is entirely located in the region extending from the element tip 1159 to the position spaced by the distance 0.8L away from the element tip 1159, when "L" represents the length of the gas receiving surface region 1013 where the solid electrolytic body 1015 is exposed to the sensing gas.

As shown in FIG. 23, the oxygen sensing element 1001 is assembled in the oxygen sensor 1003. The oxygen sensor 1003 has a portion exposed to the measuring gas and a portion exposed to the reference gas. The boundary between these portions is sealed by the oxygen sensing element 1001. The sealed portion is adjacent to the edge of the gas receiving surface region 1013 on the oxygen sensing element 1001, so as to prevent the measuring gas from advancing beyond this sealed portion.

The measuring gas flows at a reduced speed in a region exceeding the 0.8L position due to the presence of the sealed portion. If the sensing electrode 1011 is provided in this region, the sensor output will deteriorate.

Accordingly, it becomes possible to obtain an oxygen sensing element having satisfactory response by providing the sensing electrode 1011 in the region not exceeding the 0.8L position (refer to later described experimental data).

Furthermore, according to this embodiment, the sensing electrode 1011 has the thickness of 0.5~3.0 μm. This arrangement makes it possible to allow the measuring gas to diffuse and penetrate well in the sensing electrode 1011. Thus, it becomes possible to obtain an oxygen sensing element having excellent response (refer to later described experimental data).

Accordingly, this embodiment provides an oxygen sensing element which has excellent response and is capable of preventing the breaking and deterioration in the characteristics.

Figure 24:
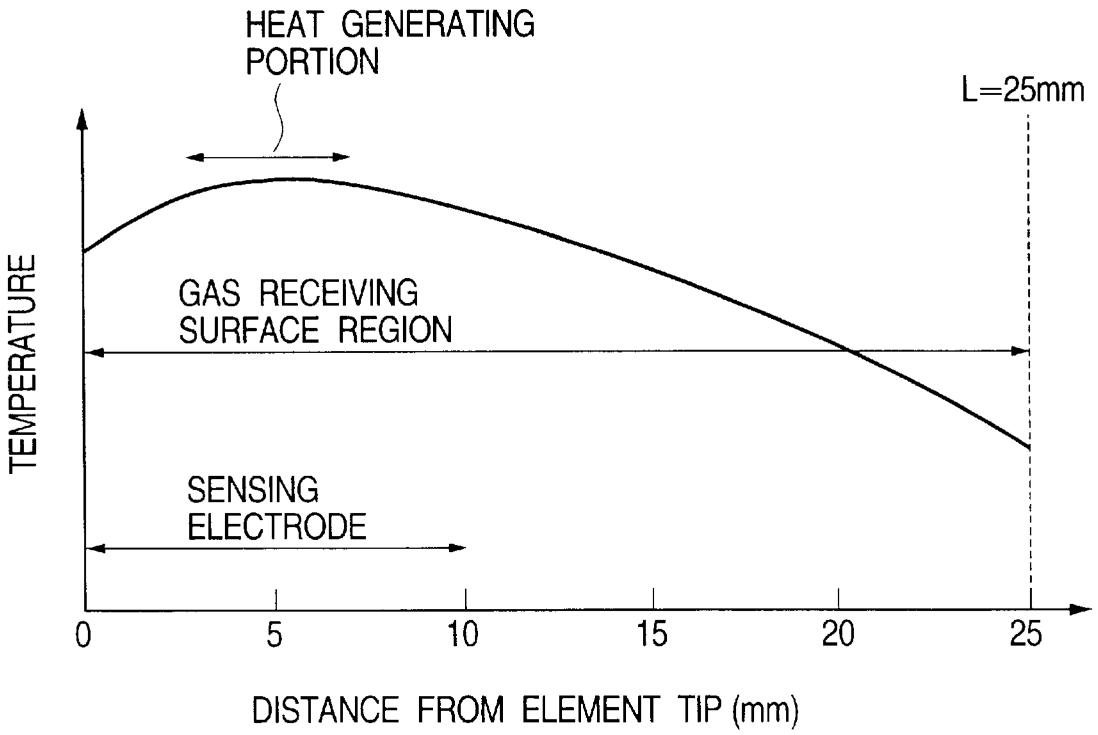
FIG. 24 is a graph showing a temperature distribution along a gas receiving surface region on the outer surface of the solid electrolytic body in relation to a distance from the element tip.

FIG. 24 shows a temperature distribution along the gas receiving surface region 1013 on the outer surface 1150 of the solid electrolytic body 1015, obtained when the oxygen sensing element 1001 is assembled in the oxygen sensor 1003 shown in FIG. 21 and installed in an exhaust passage of an internal combustion engine of an automotive vehicle, wherein the temperature of the exhaust gas is stabilized at a predetermined value (approximately 600° C.).

According to the experimental data shown in FIG. 24, it is understood that the temperature of the solid electrolytic body 1015 is high at a position corresponding to the heat generating portion 1020 of the heater 1002 and is low at a position far from the heat generating portion 1020.

According to the oxygen sensing element 1001 of this embodiment, the reference electrode 1012 is partly provided on the inner surface 1160. However, it is possible to form the reference electrode 1012 entirely on the inner surface 1160.

In this case, the inner surface 1160 is dipped into a noble metal containing organometallic solution, heat treated, and then applied the plating to obtained the reference electrode 1012 entirely formed on the inner surface 1160. Thus, the reference electrode 1012 is easily fabricated.

Figure 25A:
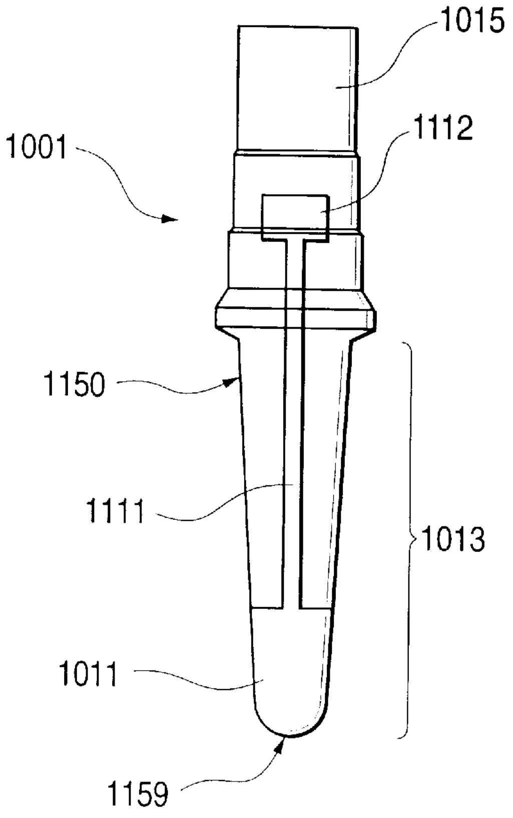
FIGS. 25A and 25B are views showing a terminal connected to a reference electrode formed on an inner surface of the oxygen sensing element in accordance with the first embodiment of the present invention.
Figure 25B:
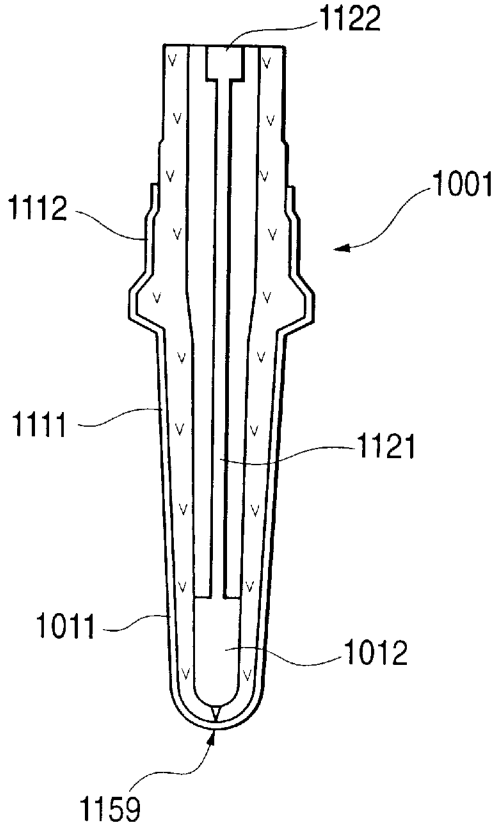

According to the oxygen sensing element 1001 of this embodiment, the terminal portion 1122 is provided on the outer surface 1150 of the solid electrolytic body 1015. It is, however, possible to provide the terminal portion 1122 on the inner surface 1160 of the solid electrolytic body 1015, as shown in FIGS. 25A and 25B.

Sensor performances were evaluated on various oxygen sensing element samples having various dimensions in each of the length L of the gas receiving surface region 1013, the length L1 of the sensing electrode 1011, and the length L2 of the heat generating portion 1020.

Table 1 shows the test result of samples 1–12 of the oxygen sensing element in accordance with the present invention. Table 2 shows the test result of comparative samples 13–20.

The samples 1–20 are different in L1, L2, L1/L2 and L values of the arrangement shown in the above-described embodiment.

Figure 30:
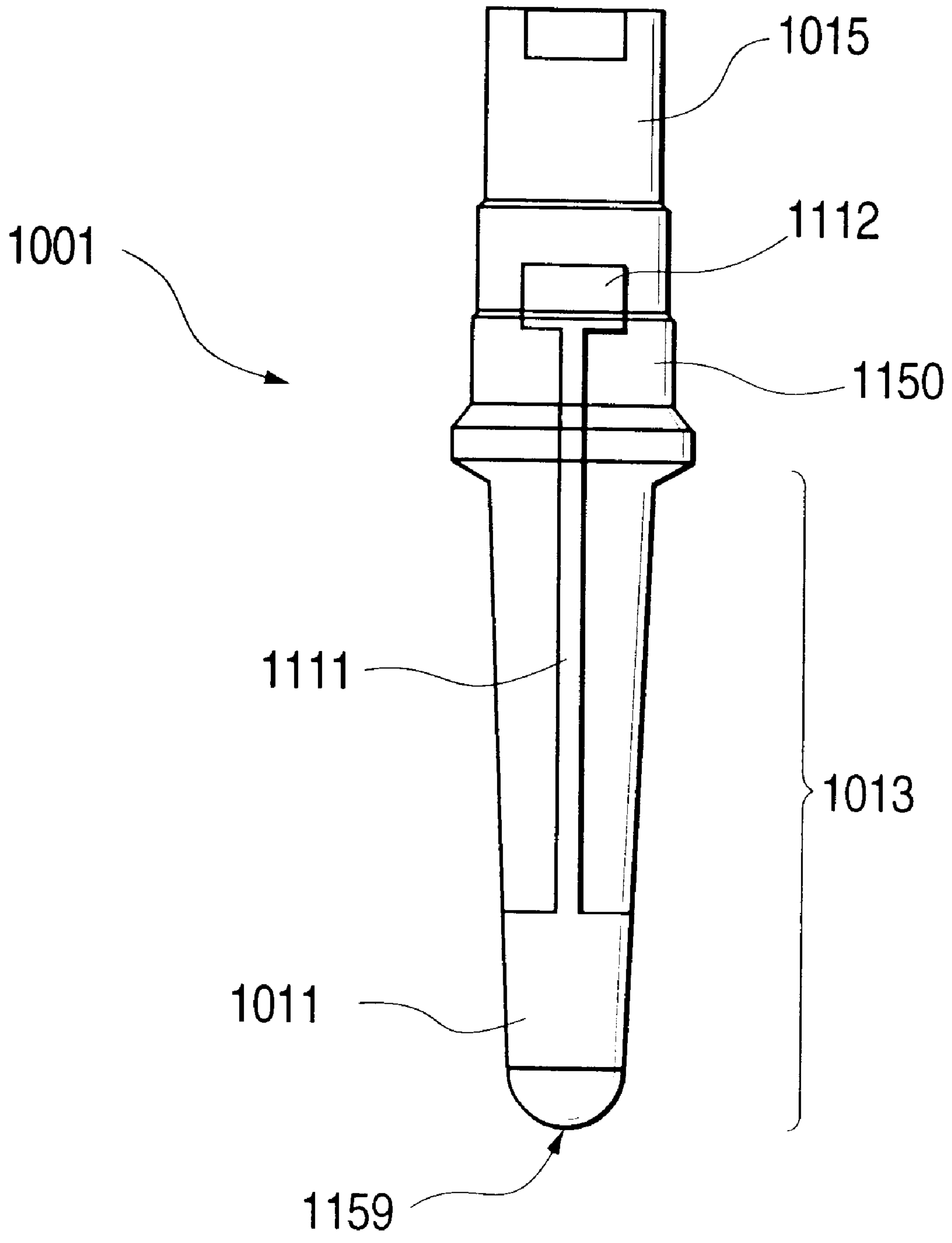
FIG. 30 is a side view showing another oxygen sensing element having a ring sensing electrode in accordance with the second embodiment of the present invention.

The sample 4 has a sensing electrode whose lower end is spaced 3 mm away from the distal end of the oxygen sensing element (refer to FIG. 30). The sample 12 has a sensing electrode fabricated by sputtering. The sample 19 has a sensing electrode formed by applying a noble-metallic containing paste and heat treating the applied paste.

The performances of each sample is measured in the following manner.

First, measurement of the response is explained.

A heater equipped oxygen sensing element was securely fixed to an exhaust passage of an internal combustion engine of an automotive vehicle. After the engine was started up, electric power (5 W) was supplied to the heater. Then, each sample was alternately subjected to rich measuring gas (λ=0.9) and lean measuring gas (λ=1.1) to check the output signal response (i.e., frequency) about a reference level of 0.45 V.

In Tables 1 and 2, ○-marked samples demonstrated satisfactory response in the sensor output frequency which is larger than 0.8 Hz. On the other hand, Δ-marked samples demonstrated the sensor output frequency in the range from 0.75 Hz to 0.8 Hz, and x-marked samples demonstrated the unsatisfactory sensor output frequency which is less than 0.75 Hz.

Second, measurement of the sensor output is explained.

Like the above-described response measurement, the heater equipped oxygen sensing element was securely fixed to the exhaust passage of the internal combustion engine of the automotive vehicle. After the engine was started up, electric power (5 W) was supplied to the heater. Then, each sample was alternately subjected to rich measuring gas (λ=0.9) and lean measuring gas (λ=1.1) to measure a sensor output difference.

The sensor output difference is another factor used in the evaluation of the response. When the sensor output frequency is identical or constant, having a large sensor output difference is regarded as excellent in the response.

In Tables 1 and 2, ○-marked samples demonstrated satisfactory response in the sensor output difference which is larger than 0.7 V. On the other hand, Δ-marked samples demonstrated the sensor output difference in the range from 0.65 Hz to 0.7 Hz, and x-marked samples demonstrated the unsatisfactory sensor output difference which is less than 0.65 Hz.

Third, measurement of the thermal durability is explained.

The thermal durability was measured through the following two tests.

(1) Each sample was left in a high-temperature environment of 900° C. for 500 hours. In Tables 1 and 2, ○-marked samples demonstrated good durability equivalent to the sensor output larger than 0.5 V. On the other hand, Δ-marked samples demonstrated the sensor output in the range from 0.4 V to 0.5 V, and x-marked samples demonstrated the unsatisfactory sensor output which is less than 0.4 V.

Figure 26:
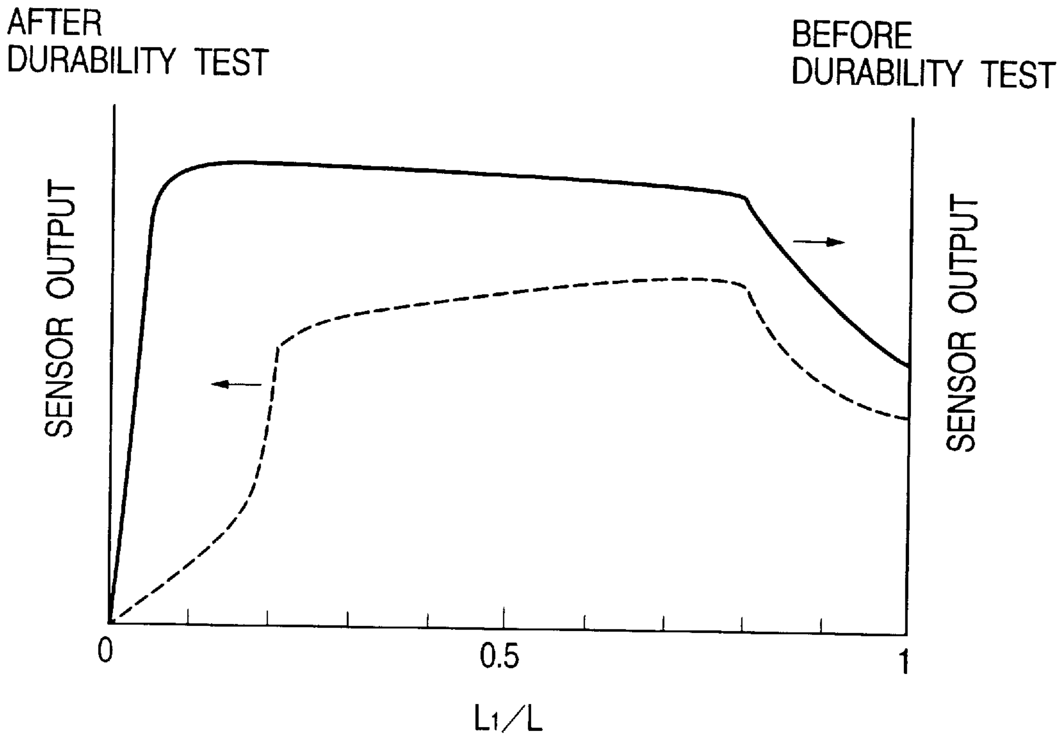
FIG. 26 is a graph showing a relationship between the sensor output and the ratio L1/L observed before and after a thermal durability test in accordance with the second embodiment of the present invention.

FIG. 26 summarizes the relationship between the sensor output and the ratio L1/L measured before and after this first durability test.

(2) Next, heater ON/OFF durability was checked by intermittently supplying electric power to the heater at the intervals of 10 seconds to 10 minutes. About 10 seconds after the start of electric power supply, the heater temperature reached 1,200° C. at the central position of the heat generating portion. A total number of repetition in each heater ON/OFF durability test reached about 10,000.

In Tables 1 and 2, ○-marked samples demonstrated good durability equivalent to the sensor output larger than 0.5 V. On the other hand, A-marked samples demonstrated the sensor output in the range from 0.4 V to 0.5 V, and x-marked samples demonstrated the unsatisfactory sensor output which is less than 0.4 V.

Figure 27:
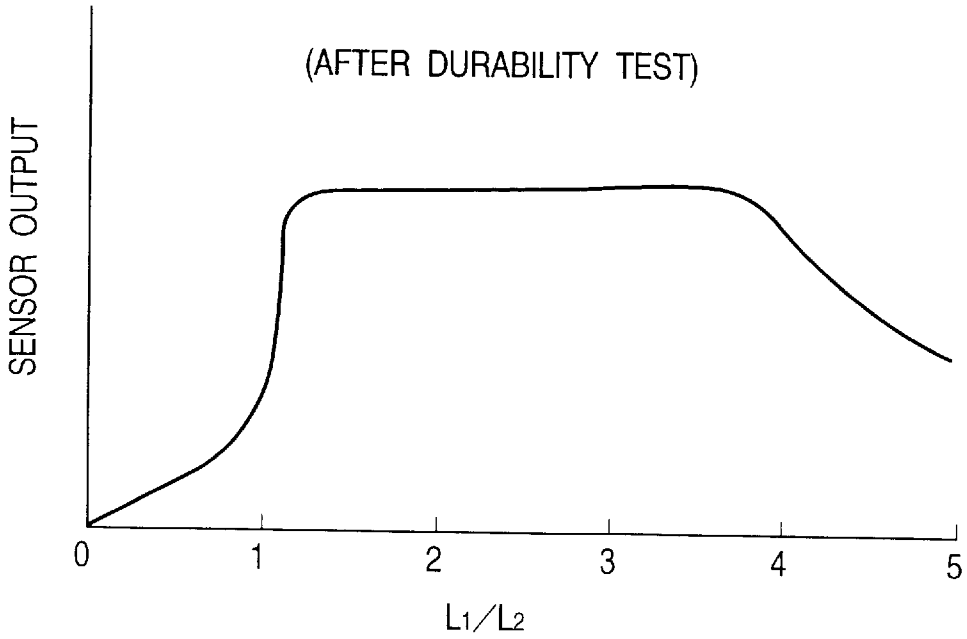
FIG. 27 is a graph showing a relationship between the sensor output and the ratio L1/L2 in accordance with the second embodiment of the present invention.

FIG. 27 summarizes the relationship between the sensor output and the ratio L1/L2 measured before and after this second durability test.

As apparent from Tables 1 and 2, samples 1~12 demonstrated excellent performances in the response, sensor output, and thermal durability. Each of these excellent samples 1~12 has the sensing electrode having the length L1 equal to or larger than 0.2L in the longitudinal direction of the oxygen sensing element 1001, entirely located in the region extending from the element tip 1159 to the position spaced by the distance 0.8L away from the element tip 1159, and having the thickness in the range of 0.5~3.0 μm.

The comparative sample 13 (L1=0.16L) was not satisfactory in the thermal durability. The comparative sample 14 having the sensing electrode extending beyond the 0.8L position was insufficient in the response and in the sensor output. The comparative samples 15 and 19, having thick sensing electrodes (3.5 μm and 5 μm), were insufficient in the response and in the sensor output. The comparative sample 16, having a thin sensing electrode, was not satisfactory in the thermal durability.

The comparative sample 17, having a large clearance, was insufficient in the response and in the sensor output. The comparative sample 18, large in the ratio L1/L2, was not satisfactory in the response and in the sensor output. The comparative sample 20, small in the ratio L1/L2, was insufficient in the thermal durability.

Furthermore, when the length L2 is equal to or larger than 0.2L, it is possible to obtain an acceptable sensor output after the durability test as shown in FIG. 26.

Moreover, when the ratio L1/L2 is in the range of 1.0~4.0, it is possible to obtain a high sensor output (i.e., excellent response) as shown in FIG. 27.

Table 3 compares the above-described sample 1 and another comparative sample 21 to check the activation time of the oxygen sensing element. The sample 21 has a heater with a long heat generating portion. Each of the samples 1 and 21 was exposed to rich exhaust gas (λ=0.9, 400° C.) emitted from the internal combustion engine of the automotive vehicle. At the same time, electric power is supplied to the heater. The activation time, i.e., a time required for the sensor to produce a 0.45 V output signal, was measured. In Table 3, the ○-marked sample demonstrated an acceptable activation time less than 25 seconds and the x-marked sample demonstrated an unacceptable activation time larger than 30 seconds As apparent from Table 3, it is understood that using a long heat generating portion takes a long time to activate the oxygen sensing element due to delay in the temperature increase in the heater.

TABLE 1-(1)

| sample No. | 1 | 2 | 3 | 4 | 5 | 6 |
|---|---|---|---|---|---|---|
| L1 (mm) | 10 (0.40L) | 10 (0.67L) | 10 (0.33L) | 10 (0.40L) | 10 (0.40L) | 10 (0.40L) |
| L2 (mm) | 4 (0.16L) | 4 (0.27L) | 4 (0.13L) | 4 (0.16L) | 4 (0.16L) | 4 (0.16L) |
| L (mm) | 25 | 15 | 30 | 25 | 25 | 25 |
| L1/L2 | 2.5 | 2.5 | 2.5 | 2.5 | 2.5 | 2.5 |
| central position (mm) | 5 | 5 | 5 | 5 | 5 | 5 |
| sensing electrode thickness (μm) | 1.5 | 1.5 | 1.5 | 1.5 | 1.0 | 3.0 |
| clearance (mm) | 0.2 | 0.2 | 0.2 | 0.2 | 0.2 | 0.2 |
| fabrication method | chemical plating | chemical plating | chemical plating | chemical plating | chemical plating | chemical plating |
| response frequency (Hz) | 0.88 ○ | 0.87 ○ | 0.85 ○ | 0.88 ○ | 0.90 ○ | 0.81 ○ |
| sensor output (V) | 0.77 ○ | 0.75 ○ | 0.74 ○ | 0.76 ○ | 0.79 ○ | 0.70 ○ |
| durability (1) | ○ | ○ | ○ | ○ | ○ | ○ |
| durability (2) | ○ | ○ | ○ | ○ | ○ | ○ |

TABLE 1-(2)

| sample No. | 7 | 8 | 9 | 10 | 11 | 12 |
|---|---|---|---|---|---|---|
| L1 (mm) | 10 (0.40L) | 10 (0.67L) | 12 (0.48L) | 5 (0.20L) | 20 (0.80L) | 10 (0.40L) |
| L2 (mm) | 4 (0.16L) | 3 (0.12L) | 12 (0.48L) | 3 (0.12L) | 5 (0.20L) | 4 (0.16L) |
| L (mm) | 25 | 25 | 25 | 25 | 25 | 25 |
| L1/L2 | 2.5 | 3.3 | 1.0 | 1.7 | 4.0 | 2.5 |
| central position (mm) | 5 | 4.5 | 9 | 4.5 | 5.5 | 5 |
| sensing electrode thickness (μm) | 1.5 | 1.5 | 1.5 | 1.5 | 1.5 | 1.5 |

TABLE 1-(2)-continued

| sample No. | 7 | 8 | 9 | 10 | 11 | 12 |
|---|---|---|---|---|---|---|
| clearance (mm) | 1.0 | 0.2 | 0.2 | 0.2 | 0.2 | 0.2 |
| fabrication method | chemical plating | chemical plating | chemical plating | chemical plating | chemical plating | sputtering |
| response | 0.80 | 0.82 | 0.82 | 0.92 | 0.81 | 0.82 |
| frequency (Hz) | ○ | ○ | ○ | ○ | ○ | ○ |
| sensor | 0.71 | 0.71 | 0.73 | 0.80 | 0.73 | 0.74 |
| output (V) | ○ | ○ | ○ | ○ | ○ | ○ |
| durability (1) | ○ | ○ | ○ | ○ | ○ | ○ |
| durability (2) | ○ | ○ | ○ | ○ | ○ | ○ |

TABLE 2

| sample No. | 13 | 14 | 15 | 16 | 17 | 18 | 19 | 20 |
|---|---|---|---|---|---|---|---|---|
| L1 (mm) | 4 (0.16L) | 21 (0.84L) | 10 (0.40L) | 10 (0.40L) | 10 (0.40L) | 17 (0.68L) | 10 (0.40L) | 10 (0.40L) |
| L2 (mm) | 4 (0.16L) | 10 (0.40L) | 4 (0.16L) | 4 (0.16L) | 4 (0.16L) | 4 (0.16L) | 4 (0.16L) | 11 (0.44L) |
| L (mm) | 25 | 25 | 25 | 25 | 25 | 25 | 25 | 25 |
| L1/L2 | 1.0 | 2.1 | 2.5 | 2.5 | 2.5 | 4.3 | 2.5 | 0.9 |
| central position (mm) | 5 | 8 | 5 | 5 | 5 | 7 | 5 | 7 |
| sensing electrode thickness ($\mu$m) | 1.5 | 1.5 | 3.5 | 0.4 | 1.5 | 1.5 | 5 | 1.5 |
| clearance (mm) | 0.2 | 0.2 | 0.2 | 0.2 | 1.1 | 0.2 | 0.2 | 0.2 |
| fabrication method | chemical plating | ← | ← | ← | ← | ← | paste | chemical plating |
| response | 0.82 | 0.77 | 0.76 | 0.89 | 0.79 | 0.77 | 0.71 | 0.82 |
| frequency (Hz) | ○ | Δ | Δ | ○ | Δ | Δ | x | ○ |
| sensor | 0.71 | 0.69 | 0.65 | 0.78 | 0.68 | 0.66 | 0.60 | 0.72 |
| output (V) | ○ | Δ | Δ | ○ | Δ | Δ | x | ○ |
| durability (1) | x | ○ | ○ | x | ○ | ○ | ○ | ○ |
| durability (2) | Δ | ○ | ○ | Δ | ○ | ○ | ○ | Δ |

TABLE 3

| sample No. | 1 | 21 |
|---|---|---|
| L1 (mm) | 10 (0.40L) | 15 (0.60L) |
| L2 (mm) | 4 (0.16L) | 15 (0.60L) |
| L (mm) | 25 | 25 |
| L1/L2 | 2.5 | 1.0 |
| central position (mm) | 5 | 10 |
| sensing electrode thickness ($\mu$m) | 1.5 | 1.5 |
| clearance (mm) | 0.2 | 0.2 |
| fabrication method | chemical plating | chemical plating |
| activation time (sec) | 20<br>○ | 32<br>x |

Figure 28:
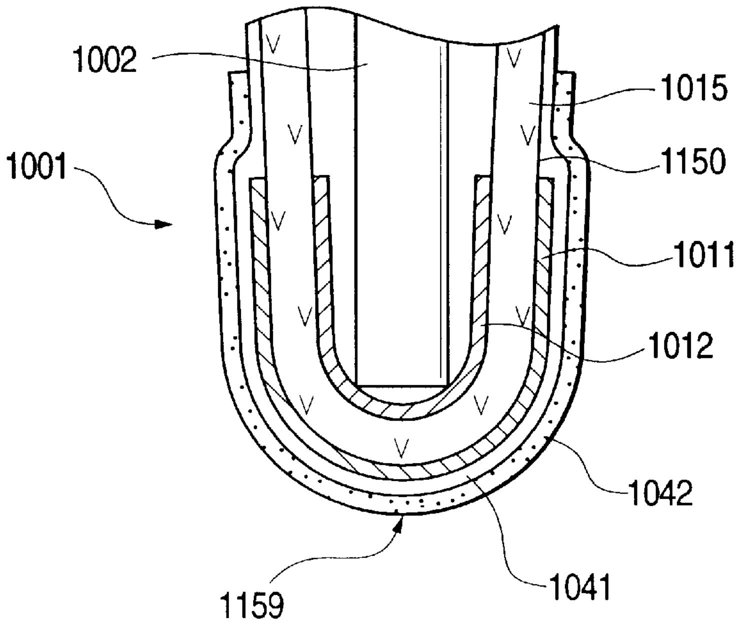
FIG. 28 is an enlarged vertical cross-sectional view showing an essential arrangement of another oxygen sensing element having two protecting layers in accordance with the second embodiment of the present invention.

FIG. 28 shows a modified oxygen sensing element 1001 having two protecting layers.

As shown in FIG. 28, the oxygen sensing element 1001 has a second protecting layer 1042 formed on the surface of the protecting layer 1041 (i.e., serving as a first protecting layer) of $MgAl_2O_4$ spinel formed entirely on the gas receiving surface region 1013 by plasma spray in the same manner as in the above-described embodiment.

The second protecting layer 1042 has a thickness of 20~60 $\mu$m and a porous rate of 20~50% and contains $Al_2O_3$. This porous rate is larger than that of the first protecting layer 1041

The second protecting layer 1042 is fabricated by dipping the surface of the first protecting layer 1041 in a slurry of $Al_2O_3$ and then heat treating the coated layer.

Effect of the second protecting layer 1042 is sufficiently obtained when the sensing electrode 1011 is covered by the second protecting layer 1042. According to this arrangement, the second protecting layer 1042 extends from the element tip 1159 to a position spaced by a distance of 12 mm (=0.48L) away from the element tip 1159. However, it is possible to enlarge the second protecting layer 1042 along the entire surface of the gas receiving surface region 1013.

According to this arrangement, the second protecting layer 1042 traps poisonous components contained in the measuring gas. Thus, it becomes possible to prevent the sensing electrode 1011 from deteriorating.

Figure 29:
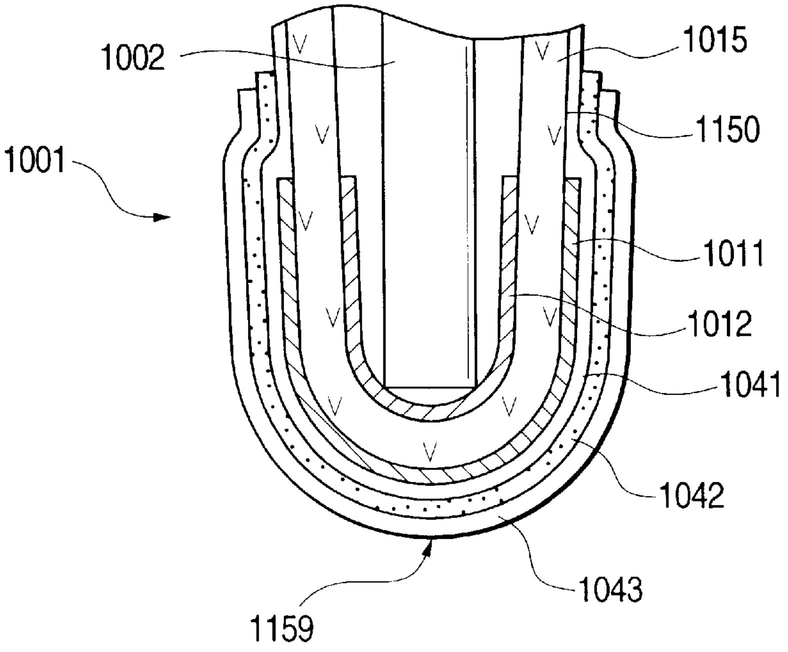
FIG. 29 is an enlarged vertical cross-sectional view showing an essential arrangement of another oxygen sensing element having three protecting layers in accordance with the second embodiment of the present invention.

FIG. 29 shows another modified oxygen sensing element 1001 having three protecting layers.

As shown in FIG. 29, the oxygen sensing element 1001 has a third protecting layer 1043 formed on the surface of the second protecting layer 1042 which is formed on the surface of the first protecting layer 1041 of $MgAl_2O_4$ spinel formed entirely on the gas receiving surface region 1013 by plasma spray in the same manner as in the above-described embodiment.

The third protecting layer 1043 has a thickness of 40 $\mu$m and a porous rate of 60%. This porous rate is larger than that of the second protecting layer 1042

Like the second protecting layer 42, the third protecting layer 1043 is fabricated by dipping the surface of the second protecting layer 1042 in the slurry of $Al_2O_3$ and then heat treating the coated layer.

Like the second protecting layer 1042, effect of the third protecting layer 1043 is sufficiently obtained when the sensing electrode 1011 is covered by the third protecting layer 1043. According to this arrangement, the third protecting layer 1043 extends from the element tip 1159 to a position spaced by a distance of 11 mm (=0.44L) away from the element tip 1159.

According to this arrangement, the third protecting layer 1043 traps large poisonous components contained in the measuring gas. This is effective to prevent the second protecting layer 1042 from being blinded by poisonous members.

FIG. 30 discloses another modified oxygen sensing element having a sensing electrode formed in a region other than the distal end of the sensing element.

As shown in FIG. 30, the oxygen sensing element 1001 has the sensing electrode 1011 whose lower end is spaced away from the element tip 1159 by an altitudinal distance of 3 mm. The upper end of the sensing electrode 1011 is located at the 0.40L (=10 mm) position.

As described in the foregoing description, the sensing electrode 1011 is connected via the lead portion 1111 to the terminal portion 1112. The lead portion 1111 has a circumferential width of 1.5 mm. The terminal portion 1112 has a circumferential width of 7 mm and a longitudinal length of 4 mm. The gas receiving surface region 1013 has the length L of 25 mm. Although not shown in the drawing, the heat generating portion 1020 of the heater 1002 has the length L2 of 4.0 mm. The central position of the heat generating portion 1020 is 5 mm away from the element tip 1159. A clearance of 0.2 mm is provided between the heater 1002 and the inner surface 1160. The sensing electrode 1011 has a thickness of 1.5 $\mu$m.

The rest is substantially the same as the arrangement disclosed in the above-described embodiment.

According to this arrangement, the distal end of the oxygen sensing element 1001 is semispherical. If the pad printing is applied, transferring a Pt paste to this semispherical portion will be difficult and it may be necessary to perform the pad printing repetitively. However, this arrangement has no electrode in the distal end region. Thus, the manufacturing is easy.

Figure 31A:
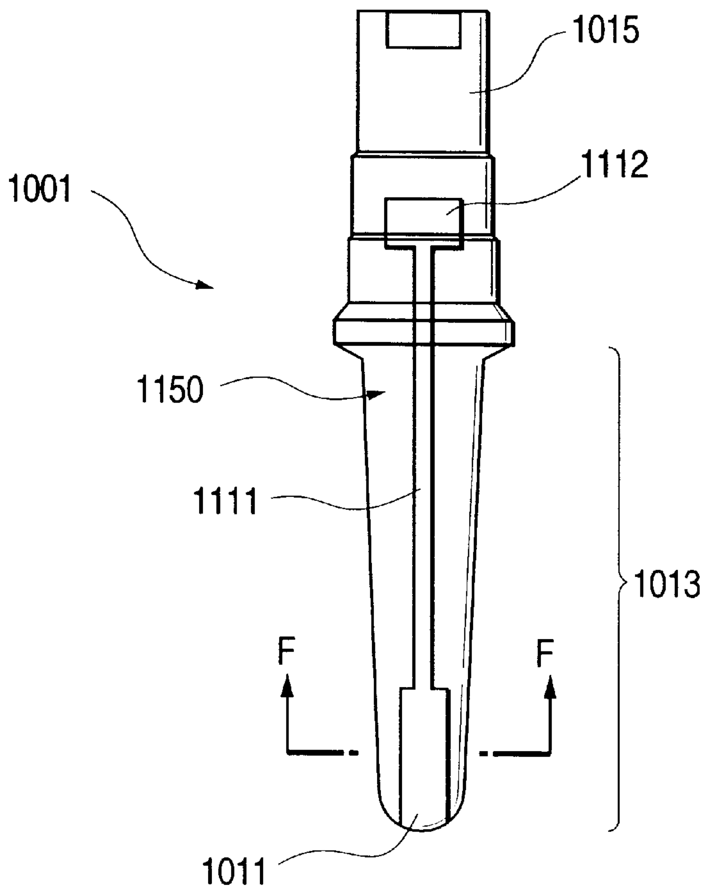
FIG. 31A is a side view showing another oxygen sensing element having a sensing electrode partly formed on its side surface in accordance with the second embodiment of the present invention.
Figure 31B:
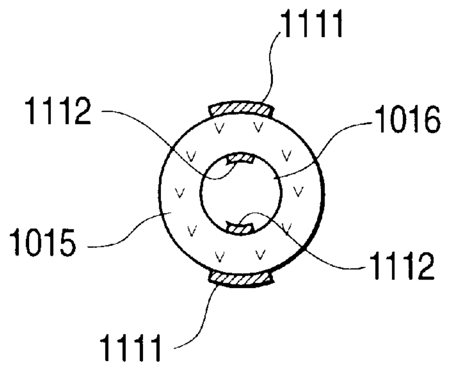
FIG. 31B is a transverse cross-sectional view taken along a line F—F of FIG. 31A.

FIGS. 31A and 31B disclose another modified oxygen sensing element having a sensing electrode partly formed on a circumferential surface of the solid electrolytic body.

As shown in FIGS. 31A and 31B, the oxygen sensing element 1001 has the sensing electrode 1011 extending from the element tip 1159 to the 0.40L (=10 mm) position. The sensing electrode 1011 has a circumferential width of 3 mm.

As described in the foregoing description, the sensing electrode 1011 is connected via the lead portion 1111 to the terminal portion 1112. The lead portion 1111 has a circumferential width of 1.5 mm. The terminal portion 1112 has a circumferential width of 7 mm and a longitudinal length of 4 mm. The gas receiving surface region 1013 has the length L of 25 mm. Although not shown in the drawing, the heat generating portion 1020 of the heater 1002 has the length L2 of 4.0 mm. The central position of the heat generating portion 1020 is located at an altitudinal distance of 5 mm from the element tip 1159. A clearance of 0.2 mm is provided between the heater 1002 and the inner surface 1160. The sensing electrode 1011 has a thickness of 1.5 $\mu$m.

The rest is substantially the same as the arrangement disclosed in the above-described embodiment.

According to this arrangement, the area of sensing electrode 1011 can be minimized. This is effective to reduce the total amount of the expensive noble metal. The manufacturing cost can be reduced.

It is possible to equalize the widths of the sensing electrode 1011, the lead portion 1111 and the terminal portion 1112.

Figure 32A:
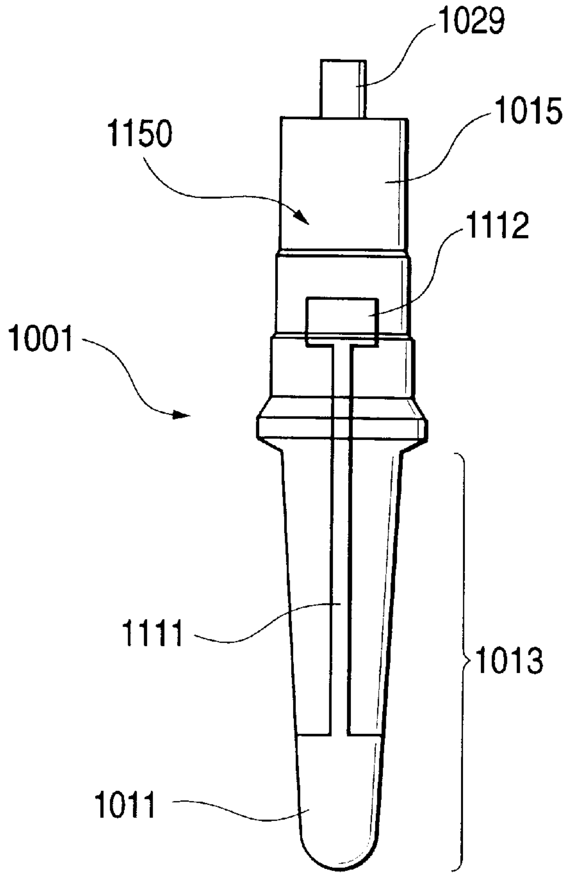
FIG. 32A is a side view showing another oxygen sensing element having a platelike heater in accordance with the second embodiment of the present invention.
Figure 32B:
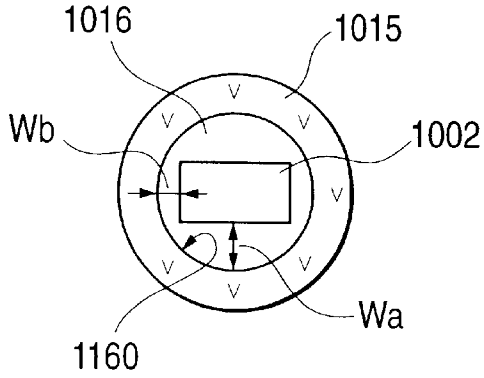
FIG. 32B is a transverse cross-sectional view showing the same.

FIGS. 32A and 32B show an oxygen sensing element having a platelike heater having a rectangular cross section.

As shown in FIG. 32A, the oxygen sensing element 1001 has the cup-shaped solid electrolytic body 1015, the sensing electrode 1011 formed on the outer surface 1150 of the solid electrolytic body 1015, and the reference gas chamber 1016 formed in the solid electrolytic body 1015.

A multilayered heater 1002, comprising a heat generating portion formed by printing on an $Al_2O_3$ substrate having a rectangular cross section, is disposed in the reference gas chamber 1016.

As shown in FIG. 32B, a clearance Wa (=1.0 mm) is provided between the wide face of the heater 1002 and the inner surface 1160 of the solid electrolytic body 1015. A clearance Wb (=0.85 mm) is provided between the narrow face of the heater 1002 and the inner surface 1160.

The heat generating portion of the heater 1002 has the length L2 of 9 mm. The central position of the heat generating portion is 7 mm away from the element tip 1159.

In this case, the clearance between the heater 1002 and the solid electrolytic body 1015 is expressed by an average of the distances from respective faces of the heater 1002. The rest is substantially the same as the arrangement disclosed in the above-described embodiment.

Figure 33:
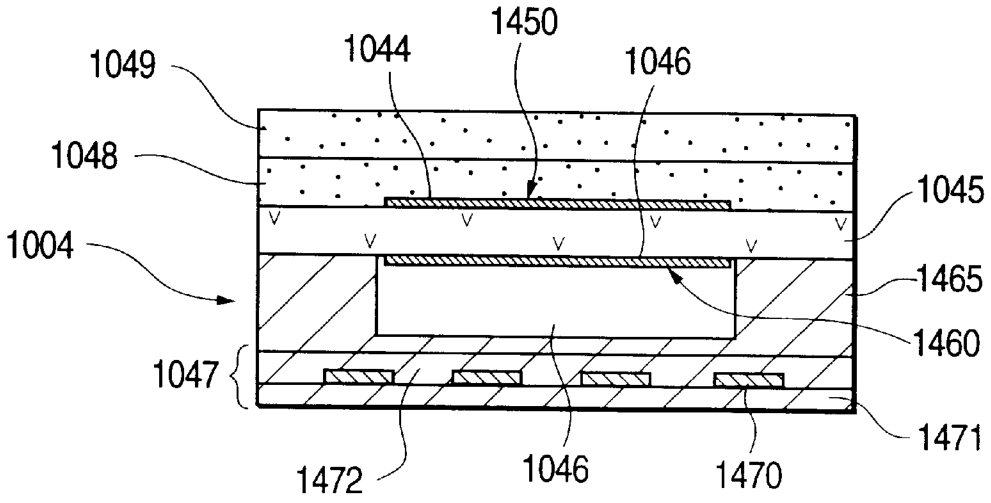
FIG. 33 is a transverse cross-sectional view showing an multilayered oxygen sensing element in accordance with the second embodiment of the present invention.
Figure 34:
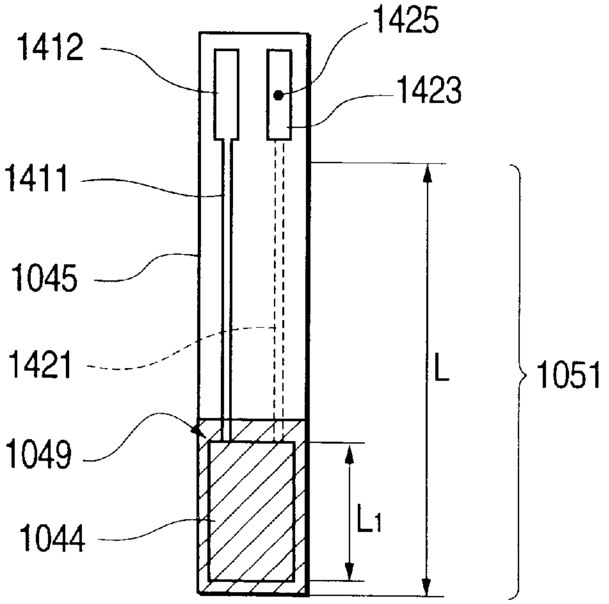
FIG. 34 is a side view showing the multilayered oxygen sensing element shown in FIG. 33.

FIGS. 33 and 34 show another multilayered oxygen sensing element which comprises a platelike solid electrolytic body 1045, a sensing electrode 1044 formed on an outer surface 1450 of the solid electrolytic body 1045, and a reference electrode 1046 formed on an inside surface 1460 of the solid electrolytic body 1045. A first protecting layer 1048 and a second protecting layer 1049 cover the upper surface of the sensing electrode 1044. The sensing electrode 1044 and the reference electrode 1046 are fabricated by the same method as that disclosed in the above-described embodiment.

A spacer 1465 is stacked on the inner surface 1460 of the solid electrolytic body 1045 so as to define a reference gas chamber. A heater 1047 is stacked on the spacer 1465. The heater 1047 comprises a heater substrate 1471 of $Al_2O_3$ ceramic sheet, a plurality of heat generating elements 1470 disposed on the surface of the heater substrate 47, and a cover substrate 1472 covering the heat generating elements 470. The heater substrate 1471 can be fabricated by press forming, injection forming or sheet forming.

A lead portion 1411 and a terminal portion 1412 are formed on the outer surface 1450 of the solid electrolytic body 1045 to transmit a sensing signal from the sensing electrode 1044.

A lead portion 1421 is formed on the inner surface 1460 of the solid electrolytic body 1045 to transmit a reference signal from the reference electrode 1046. The lead portion 1421 is electrically connected to a terminal 1423 formed on the outer surface 1450 via a through hole 1425.

The sensing electrode 1044 is 8 mm in length L1 and 4 mm in width. The heat generating portion of the heater 1047 is 7 mm in length L2 and 5 mm in width.

The sensing electrode 1044 is spaced by a distance of 1 mm away from the distal end of the solid electrolytic body 1045. The central position of the heat generating portion is 5 mm away from the distal end of the solid electrolytic body 1045. The gas receiving surface region 1051 has a length L of 20 mm. Th rest is substantially the same as the arrangement disclosed in the above-described embodiment.

According to this arrangement, the oxygen sensing element 1004 has a short activation time because the heater 1047 and the solid electrolytic body 1045 are integrated.

The present invention can be applied to any other multilayered oxygen sensing element, such as a 2-cell type multilayered oxygen sensing element comprising a plurality of solid electrolytic layers.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. An oxygen sensing element comprising a cup-shaped solid electrolytic body with one end closed and an inside space serving as a reference gas chamber, a sensing electrode provided on an outer surface of said solid electrolytic body so as to be exposed to measuring gas, a reference electrode provided on an inner surface of said solid electrolytic body, and a heater disposed in said reference gas chamber, wherein a contact portion comprises a region where said heater is brought into contact with said inner surface of said solid electrolytic body and an opposing region on the outer surface of said solid electrolytic body, said sensing electrode includes at least part of said contact portion, a gas receiving surface region, exposed to the measuring gas when said oxygen sensing element is operated, is provided on the outer surface of said oxygen sensing element so as to extend from a distal end of said oxygen sensing element to a position spaced by a distance L away from said distal end, at least part of said contact portion is located in a region extending from said distal end of said oxygen sensing element to a position spaced by a distance 0.4L away from said distal end, and said sensing electrode is entirely located in a region extending from said distal end of said oxygen sensing element to a position spaced by a distance 0.8L away from said distal end.

2. The oxygen sensing element in accordance with claim 1, wherein said sensing electrode and said reference electrode are in a confronting relationship via said solid electrolytic body.

3. The oxygen sensing element in accordance with claim 1, wherein an external lead electrode extends on said outer surface of said solid electrolytic body to transmit a sensing signal of said sensing electrode to the outside, and said external lead electrode has a circumferential width in a range from 0.1 mm to 5 mm.

4. The oxygen sensing element in accordance with claim 1, wherein an internal lead electrode extends on said inner surface of said solid electrolytic body to transmit a reference signal of said reference electrode to the outside, and said internal lead electrode and said external lead electrode are in an offset relationship via said solid electrolytic body.

5. The oxygen sensing element in accordance with claim 1, wherein said sensing electrode is formed by chemical plating.

6. An oxygen sensing element comprising a solid electrolytic body, a reference gas chamber provided in said solid electrolytic body, a sensing electrode provided on an outer surface of said solid electrolytic body, a reference electrode provided on an inner surface of said solid electrolytic body which defines said reference gas chamber, wherein a gas receiving surface region, exposed to measuring gas when said oxygen sensing element is operated, is provided on the outer surface of said oxygen sensing element so as to extend from a distal end of said oxygen sensing element to a position spaced by a distance L away from said distal end, said sensing electrode has a length L1 equal to or larger than 0.2L in a longitudinal direction of said oxygen sensing element, said sensing electrode is entirely located in a region extending from said distal end of said oxygen sensing element to a position spaced by a distance 0.8L away from said distal end, and said sensing electrode has a thickness of 0.5~3.0 $\mu$m.

7. The oxygen sensing element in accordance with claim 6, wherein said oxygen sensing element has a heater which comprises a heat generating portion generating heat in response to supplied electric power, said sensing electrode is located at a position opposing to at least a central position of said heat generating portion in the longitudinal direction of said oxygen sensing element, and said heat generating portion has a length L2 in the longitudinal direction of said oxygen sensing element, so as to satisfy the relationship $1.0 \leqq L1/L2 \leqq 4.0$.

8. The oxygen sensing element in accordance with claim 6, wherein said heat generating portion has a length L2 of 3~12 mm.

9. The oxygen sensing element in accordance with claim 6, wherein the length L of said gas receiving surface region is in a range of 15~30 mm.

10. The oxygen sensing element in accordance with claim 6, wherein said sensing electrode is fabricated by chemical plating.

11. The oxygen sensing element in accordance with claim 6, wherein said reference electrode and said sensing electrode are in an opposed relationship via said solid electrolytic body.

12. The oxygen sensing element in accordance with claim 6, wherein said solid electrolytic body is a cup-shaped body having one end closed and having an inner space serving as said reference gas chamber, and said heater is accommodated in said reference gas chamber.

13. The oxygen sensing element in accordance with claim 12, wherein a clearance of 0.05~1.0 mm is provided between said heater and the inner surface of said solid electrolytic body at a longitudinal position corresponding to said sensing electrode.

14. The oxygen sensing element in accordance with claim 6, wherein said oxygen sensing element is a multilayered sensing element, and said heater and said solid electrolytic body are accumulated layers of said multilayered sensing element.

* * * * *

UNITED STATES PATENT AND TRADEMARK OFFICE

CERTIFICATE OF CORRECTION

PATENT NO. : 6,354,134 C1
APPLICATION NO. : 90/010308
DATED : September 28, 2010
INVENTOR(S) : Tooru Katafuchi et al.

It is certified that error appears in the above-identified patent and that said Letters Patent is hereby corrected as shown below:

Title page, item (54) Title should read "OXYGEN SENSING ELEMENT USED IN AN OXYGEN SENSOR"

Col. 2, line 4, should read "*which is* exposed to the measuring gas when said oxygen"

Col. 3, line 6, should read "3 [~] *to* 12 mm *in the longitudinal direction.*"

Signed and Sealed this
Fourth Day of January, 2011

David J. Kappos
*Director of the United States Patent and Trademark Office*

US006354134C1

(12) EX PARTE REEXAMINATION CERTIFICATE (7777th)

United States Patent

Katafuchi et al.

(10) Number: US 6,354,134 C1

(45) Certificate Issued: Sep. 28, 2010

(54) OXYGEN SENSING ELEMENT USED IN A OXYGEN SENSOR

(75) Inventors: Tooru Katafuchi, Kariya (JP); Kiyomi Kobayashi, Kuwana (JP); Namitsugu Fujii, Yokkaichi (JP); Hiromi Sano, Nagoya (JP)

(73) Assignee: Denso Corporation, Kariya, Aichi-Pref. (JP)

Reexamination Request:
No. 90/010,308, Oct. 7, 2008

Reexamination Certificate for:

| | |
|---|---|
| Patent No.: | **6,354,134** |
| Issued: | **Mar. 12, 2002** |
| Appl. No.: | **09/196,129** |
| Filed: | **Nov. 20, 1998** |

(30) Foreign Application Priority Data

Nov. 20, 1997 (JP) .............................................. 9-337869
Sep. 4, 1998 (JP) .............................................. 10-251054

(51) Int. Cl.
*G01N 27/407* (2006.01)

(52) U.S. Cl. ........................................ 73/23.32; 60/276

(58) Field of Classification Search ........................ None
See application file for complete search history.

(56) References Cited

U.S. PATENT DOCUMENTS

| | | | | |
|---|---|---|---|---|
| 5,203,983 A | | 4/1993 | Ohyama et al. | |
| 5,393,397 A | | 2/1995 | Fukaya et al. | |
| 5,662,786 A | | 9/1997 | Friese et al. | |
| 5,690,800 A | | 11/1997 | Friese et al. | |
| 5,804,050 A | | 9/1998 | Hayakawa et al. | |
| 6,096,372 A | | 8/2000 | Nomura | |
| 6,258,233 B1 | * | 7/2001 | Sugiyama et al. | 204/424 |
| 6,432,289 B1 | | 8/2002 | Uchida et al. | |

FOREIGN PATENT DOCUMENTS

| | | |
|---|---|---|
| DE | 19532158 | 3/1996 |
| DE | 19802352 | 7/1998 |
| EP | 0125069 | 11/1984 |
| EP | 0311353 | 4/1989 |
| EP | 0748441 | 12/1996 |
| EP | 0809101 | 11/1997 |
| EP | 0896219 | 2/1999 |
| JP | 57-166556 A | 10/1982 |
| JP | S59-065757 | 4/1984 |
| JP | S59-217156 | 12/1984 |
| JP | UM-S61-146762 | 7/1986 |
| JP | A-S63-003252 | 1/1988 |
| JP | 1-153953 A | 6/1989 |
| JP | A-H01-203963 | 8/1989 |

(Continued)

OTHER PUBLICATIONS

Submission of Information dated Jul. 4, 2006, re JP–A–H09–337869.

Notification of Reasons for Rejection dated Jul. 25, 2006, re JP–A–H09–337869.

Submission of Information dated Dec. 26, 2006, re JP–A–H09–337869.

(Continued)

*Primary Examiner*—Anjan K. Deb

(57) ABSTRACT

A solid electrolytic body has an inside space serving as a reference gas chamber. A sensing electrode and a reference electrode are formed on the surface of the solid electrolytic body. A heater is disposed in the reference gas chamber. A contact portion comprises a region where the heater is brought into contact with the inner surface of the solid electrolytic body and an opposing region on the outer surface of the solid electrolytic body. The sensing electrode includes at least part of the contact portion. A gas receiving surface region, exposed to the measuring gas, extends from an element tip to a position spaced by a distance L away from the element tip. At least part of the contact portion is located in a region extending from the element tip to a position spaced by a distance 0.4L away from the element tip. The sensing electrode is entirely located in a region extending from the element tip to a position spaced by a distance 0.8L away from the element tip.

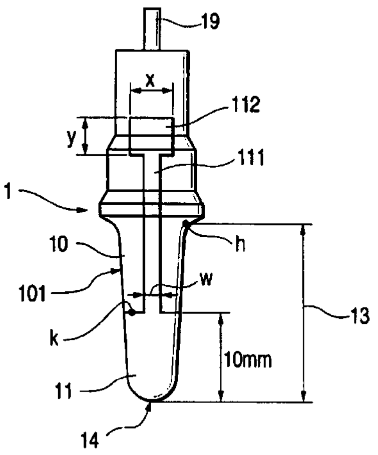

FOREIGN PATENT DOCUMENTS

| | | | |
|---|---|---|---|
| JP | H01-267448 | | 10/1989 |
| JP | 4-157358 | A | 5/1992 |
| JP | H05126787 | | 5/1993 |
| JP | A-H06-201641 | | 7/1994 |
| JP | H07-098294 | | 4/1995 |
| JP | H07-190986 | | 7/1995 |
| JP | H08-122297 | | 5/1996 |
| JP | 2545050 | B2 | 7/1996 |
| JP | 8-271474 | A | 10/1996 |
| JP | 2589136 | B2 | 12/1996 |
| JP | H09-501776 | | 2/1997 |
| JP | H09-072876 | | 3/1997 |
| JP | H09-506977 | | 7/1997 |
| JP | H09-203718 | | 8/1997 |
| JP | H09-229900 | | 9/1997 |
| JP | H09-257744 | | 10/1997 |
| JP | H09-510298 | | 10/1997 |
| JP | H09-304337 | | 11/1997 |
| JP | H10-054822 | | 2/1998 |
| JP | H10-096707 | | 4/1998 |
| JP | H10-206378 | | 8/1998 |
| WO | 96/21147 | A1 | 7/1996 |

OTHER PUBLICATIONS

Notification of Reasons for Rejection dated Jan. 9, 2007, re JP–A–H09–337869.

Notification of Reasons for Rejection dated Feb. 12, 2008, re JP–A–H09–337869.

Office Action dated Sep. 16, 2009 in Japanese Patent Application No. 2008–018814 with English spot translation of the official communication.

Submission of Information dated Jun. 10, 2008, re JP–A–H09–337869.

Decision of Refusal dated Jun. 24, 2008, re JP–A–H09–337869.

Report on Reconsideration by Examiner before Appeal dated Apr. 14, 2009, re JP–A–H09–337869.

Submission of Information dated Jul. 4, 2006, re JP–A–H10–251054.

Submission of Information dated Jan. 9, 2007, re JP–A–H10–251054.

Notification of Reasons for Rejection dated Oct. 23, 2007, re JP–A–H10–251054.

Submission of Information dated Feb. 26, 2008, re JP–A–H10–251054.

Notification of Reasons for Rejection dated May 20, 2008, re JP–A–H10–251054.

Decision on Dismissal of Amendment dated Jan. 6, 2009, re JP–A–H10–251054.

Decision on Refusal dated Jan. 6, 2009, re JP–A–H10–251054.

Submission of Information dated Jan. 27, 2009, re JP–A–2008–214907.

Submission of Information dated Jan. 27, 2009, re JP–A–2008–214908.

Official Communication dated Aug. 29, 2000 re EP 98121974.4 (EP Search Report).

Official Communication dated Jun. 11, 2001, re EP 98121974.4 (Examination Report).

Official Communication dated Feb. 19, 2002, re EP 98121974.4 (Examination Report).

Nullity Suit dated Nov. 7, 2008, with English translation and agent's lettter re EP 98121974.4.

Official Letter of the Federal Patent Court dated Jan. 8, 2009, with agent's letter re EP 98121974.4.

Official Communication dated Feb. 20, 2002, re EP 01129596.1 (EP Search Report).

Official Communication dated Mar. 24, 2005, re EP 01129596.1 (Examination Report).

Official Communication dated Nov. 29, 2005, re EP 01129596.1 (Third Party Observations).

Official Communication dated Feb. 14, 2007, re EP 01129596.1 (Third Party Observations).

Official Communication dated Feb. 14, 2007, re EP 01129596.1 (Third Party Observations).

Official Communication dated Mar. 7, 2007, with agent's letter re EP 011229596.1 (Decision to Refuse).

Official Communication dated Jul. 31, 2007, re EP 01129596.1 (Third Party Observations).

Identification of 338 pages of documents dated from Dec. 21, 1998, through Aug. 8, 2007, re EP 01129596.1 (2 pages).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 16, lines 63-67:

The sample 9 differs from the sample 1 in the condition of the reference electrode. According to the sample 9, the sensing electrode and the [sensing] *reference* electrode are disposed in an opposed relationship. The sample 9 is slightly excellent than the sample 1 in the response and the sensor output.

AS A RESULT OF REEXAMINATION, IT HAS BEEN DETERMINED THAT:

Claims 4 and 7 are cancelled.

Claims 1-3, 6, 8, 9 and 11-14 are determined to be patentable as amended.

Claims 5 and 10, dependent on an amended claim, are determined to be patentable.

Claim 4 was not reexamined.

1. An oxygen sensing element*, which is formed to have a longitudinal direction and a distal end in the longitudinal direction, the oxygen sensing element* comprising*:* a cup-shaped solid electrolytic body [with] *having an outer surface,* one end closed *in the longitudinal direction,* and an inside space [serving] *formed by an inner surface to serve* as a reference gas chamber[,]*;* a sensing electrode provided on [an] *the* outer surface of said solid electrolytic body so as to be exposed to measuring gas[,] *;* a reference electrode provided on [an] *the* inner surface of said solid electrolytic body[, and]*;* a heater disposed in said reference gas chamber[,]*;*

*an internal lead electrode formed to extend on said inner surface to transmit a reference signal from said reference electrode to the outside; and*

*an external lead electrode formed to extend on said outer surface to transmit a sensing signal from said sensing electrode to the outside,* wherein

*said solid electrolytic body has* a contact portion [comprises] *including both* a region where said heater is brought into contact with said inner surface of said solid electrolytic body and an opposing region on the outer surface of said solid electrolytic body*, the opposing region opposing the region where said heater is brought into contact with said inner surface of said solid electrolytic body*, said sensing electrode *is disposed on the outer surface area that* includes at least part of said contact portion,

*said outer surface has* a gas receiving surface region[,] *which is* exposed to the measuring as when said oxygen sensing element is operated, [is provided on the outer surface of said oxygen sensing element so as] *and formed* to extend from [a] *the* distal end of said oxygen sensing element to a position spaced *on the oxygen sensing element* by a distance L away from said distal end *in the longitudinal direction*, [and]

said sensing electrode is entirely located in a region extending from said distal end of said oxygen sensing element to a position *on the oxygen sensing element* spaced by a distance 0.8L away from said distal end *in the longitudinal direction, and*

*said internal lead electrode and said external lead electrode are offset from each other with said solid electrolytic body located therebetween.*

2. The oxygen sensing element in accordance with claim 1, wherein said sensing electrode and said reference electrode [are in a confronting relationship via] *confront each other with* said solid electrolytic body *located therebetween.*

3. The oxygen sensing element in accordance with claim 1, wherein [an external lead electrode extends on said outer surface of said solid electrolytic body to transmit a sensing signal of said sensing electrode to the outside, and] said external lead electrode has a circumferential width in a range from 0.1 mm to 5 mm *in a circumferential direction along a plane perpendicular to the longitudinal direction.*

6. An oxygen sensing element*, which is formed to have a longitudinal direction and a distal end in the longitudinal direction, the oxygen sensing element* comprising*:* a solid electrolytic body[,] *having an outer surface and an inner surface;* a reference gas chamber provided in said solid electrolytic body[,] *;* a sensing electrode provided on [an] *the* outer surface of said solid electrolytic body[,] *; and* a reference electrode provided on [an] *the* inner surface of said solid electrolytic body [which defines]*, the inner surface defining* said reference gas chamber, wherein

*said outer surface has* a gas receiving surface region[,] *which is* exposed to measuring gas when said oxygen sensing element is operated, [is provided on the outer surface of said oxygen sensing element so as to] *and which* extend*s* from [a] *the* distal end of said oxygen sensing element to a position *on the oxygen sensing element* spaced by a distance L away from said distal end *in the longitudinal direction*, said sensing electrode has a length L1 equal to or larger than 0.2L in [a] *the* longitudinal direction [of said oxygen sensing element], said sensing electrode is entirely located in a region extending from [said] *the* distal end of said oxygen sensing element to a position *on the oxygen sensing element* spaced by a distance 0.8L away from the [said] distal end *in the longitudinal direction*, [and]

said sensing electrode has a thickness of 0.5 [~] *to* 3.0 μm,

*said oxygen sensing element has a heater which comprises a heat generating portion generating heat in response to supplied electric power,*

*said sensing electrode is located at a position opposing at least a central position of said heat generating portion in the longitudinal direction, and*

*said heat generating portion has a length L2 in the longitudinal direction, the length L2 satisfying the relationship 1.0≦L1/L2≦4.0.*

8. The oxygen sensing element in accordance with claim 6, wherein said heat generating portion has a length L2 of 3[~] *to* 12 μm *in the longitudinal direction*.

9. The oxygen sensing element in accordance with claim 6, wherein the length L of said gas receiving surface region is in a range of 15[~] *to* 30 mm.

11. The oxygen sensing element in accordance with claim 6, wherein said reference electrode and said sensing electrode are [in an opposed relationship via] *opposed to each other with* said solid electrolytic body *located therebetween*.

12. The oxygen sensing element in accordance with claim 6, wherein said solid electrolytic body is a cup-shaped *solid electrolytic* body having one end closed and having an inner surface serving as said reference gas chamber, and said heater is accommodated in said reference gas chamber.

13. The oxygen sensing element in accordance with claim 12, wherein a clearance of 0.05[~] *to* 1.0 mm is provided between said heater and the inner surface of said solid electrolytic body at a longitudinal position corresponding to said sensing electrode *in the longitudinal direction*.

14. The oxygen sensing element in accordance with claim 6, wherein said oxygen sensing element is a multilayered sensing element, and said heater and said solid electrolytic body [are] *comprise* accumulated layers of said multilayered sensing element.

* * * * *